(12) United States Patent
Nanavati et al.

(10) Patent No.: US 10,772,886 B2
(45) Date of Patent: Sep. 15, 2020

(54) CXCR-2 INHIBITORS FOR TREATING CRYSTAL ARTHROPATHY DISORDERS

(71) Applicant: ARDEA BIOSCIENCES, INC., San Diego, CA (US)

(72) Inventors: Payal Nanavati, San Diego, CA (US); Jeffrey Miner, San Diego, CA (US)

(73) Assignee: ARDEA BIOSCIENCES, INC., San Diego, CA (US)

( * ) Notice: Subject to any disclaimer, the term of this patent is extended or adjusted under 35 U.S.C. 154(b) by 133 days.

(21) Appl. No.: 15/516,465

(22) PCT Filed: Mar. 9, 2017

(86) PCT No.: PCT/US2017/021570
§ 371 (c)(1),
(2) Date: Apr. 3, 2017

(87) PCT Pub. No.: WO2017/156270
PCT Pub. Date: Sep. 14, 2017

(65) Prior Publication Data
US 2018/0235964 A1    Aug. 23, 2018

Related U.S. Application Data

(60) Provisional application No. 62/307,348, filed on Mar. 11, 2016.

(51) Int. Cl.
| | | |
|---|---|---|
| A61K 31/506 | (2006.01) | |
| A61P 19/02 | (2006.01) | |
| A61K 31/165 | (2006.01) | |
| C07D 403/12 | (2006.01) | |
| A61K 45/06 | (2006.01) | |

(52) U.S. Cl.
CPC .......... *A61K 31/506* (2013.01); *A61K 31/165* (2013.01); *A61K 45/06* (2013.01); *A61P 19/02* (2018.01); *C07D 403/12* (2013.01); *A61K 2300/00* (2013.01)

(58) Field of Classification Search
None
See application file for complete search history.

(56) References Cited

U.S. PATENT DOCUMENTS

| | | |
|---|---|---|
| 7,964,647 B2 | 6/2011 | Davis et al. |
| 7,981,938 B2 | 7/2011 | Davis |
| 8,735,413 B2 | 5/2014 | Connolly et al. |
| 8,748,603 B2 | 6/2014 | Gullberg et al. |
| 2008/0096860 A1 | 4/2008 | Cheshire et al. |
| 2008/0279822 A1 | 11/2008 | Hu et al. |
| 2009/0042887 A1 | 2/2009 | Lademacher et al. |
| 2009/0093548 A1 | 4/2009 | Davis et al. |
| 2010/0093636 A1 | 4/2010 | Schultz et al. |
| 2011/0044988 A1 | 2/2011 | Bernhagen et al. |

(Continued)

FOREIGN PATENT DOCUMENTS

| | | |
|---|---|---|
| WO | WO-2004011443 A1 | 2/2004 |
| WO | WO-2006024823 A1 | 3/2006 |

(Continued)

OTHER PUBLICATIONS

Dwyer et al. CXCR2 modulators: a patent review (2009-2013). Expert Opin Ther Patents 24(5):519-534 (2014).
Norman. Evidence on the identity of the CXCR2 antagonist AZD-5069. Expert Opin Ther Pat 23(1):113-117 (2013).
PCT/US2017/021570 International Search Report and Written Opinion dated Jun. 5, 2017.
Terkeltaub et al. The murine homolog of the interleukin-8 receptor CXCR-2 is essential for the occurrence of neutrophilic inflammation in the air pouch model of acute urate crystal-induced gouty synovitis. Arthritis Rheum 41(5):900-909 (1998).

(Continued)

*Primary Examiner* — Savitha M Rao
*Assistant Examiner* — Gregg Polansky
(74) *Attorney, Agent, or Firm* — Wilson Sonsini Goodrich & Rosati

(57) ABSTRACT

N-(2-((2,3-difluorobenzyl)thio)-6-(((2R,3S)-3,4-dihydroxybutan-2-yl)oxy)pyrimidin-4-yl)azetidine-1-sulfonamide (compound 3) and N-(6-(((2R,3S)-3,4-dihydroxybutan-2-yl)oxy)-2-((4-fluorobenzyl)thio)pyrimidin-4-yl)-3-methyl-azetidine-1-sulfonamide (compound 4) are known chemokine modulators and are therefore useful in the treatment of diseases/conditions in which modulation of chemokine receptor activity is beneficial. In particular, provided herein are compositions and methods for the treatment and prevention of gout.

Compound 3

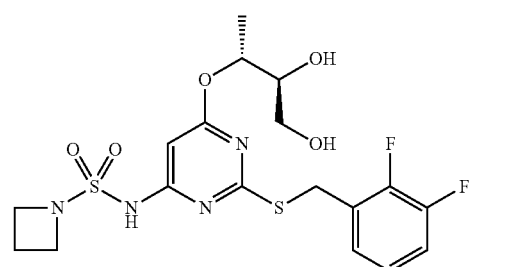

Compound 4

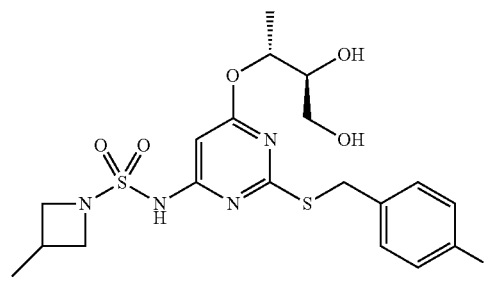

11 Claims, 8 Drawing Sheets

(56) References Cited

U.S. PATENT DOCUMENTS

| | | | |
|---|---|---|---|
| 2011/0124619 | A1 | 5/2011 | Cheshire et al. |
| 2011/0262386 | A1 | 10/2011 | Bernhagen et al. |
| 2012/0083445 | A1 | 4/2012 | Tseng et al. |
| 2012/0157431 | A1 | 6/2012 | Cheshire et al. |
| 2013/0012490 | A1 | 1/2013 | Cheshire et al. |
| 2013/0040926 | A1 | 2/2013 | Connolly et al. |
| 2013/0203991 | A1 | 8/2013 | Cheshire et al. |
| 2014/0212429 | A1 | 7/2014 | Campbell et al. |
| 2014/0228339 | A1 | 8/2014 | Connolly et al. |
| 2014/0256678 | A1 | 9/2014 | Maeda et al. |
| 2015/0166624 | A1 | 6/2015 | Tseng et al. |
| 2016/0108023 | A1 | 4/2016 | Connolly et al. |
| 2018/0221312 | A1 | 8/2018 | Nanavati et al. |

FOREIGN PATENT DOCUMENTS

| | | | |
|---|---|---|---|
| WO | WO-2009039091 A1 | | 3/2009 |
| WO | WO-2009073683 A2 | | 6/2009 |
| WO | WO-2010007427 A1 | | 1/2010 |
| WO | WO-2010056399 A1 | | 5/2010 |
| WO | WO-2010065491 A2 | | 6/2010 |
| WO | WO-2010071865 A1 | | 6/2010 |
| WO | WO-2011038149 A2 | | 3/2011 |
| WO | WO-2011116245 A2 | | 9/2011 |
| WO | WO-2012007748 A1 | | 1/2012 |
| WO | WO 2013/008002 A1 | * | 1/2013 |
| WO | WO-2013008002 A1 | | 1/2013 |
| WO | WO-2016079049 A1 | | 5/2016 |
| WO | WO-2017156270 A1 | | 9/2017 |
| WO | WO-2019055509 A1 | | 3/2019 |

OTHER PUBLICATIONS

Bou-Dargham et al. The Role of Interleukin-1 in Inflammatory and Malignant Human Skin Diseases and the Rationale for Targeting Interleukin-1 Alpha. Med Res Rev 37(1):180-216 (2017).

Carretero et al. Differential Features between Chronic Skin Inflammatory Diseases Revealed in Skin-Humanized Psoriasis and Atopic Dermatitis Mouse Models. J Invest Dermatol 136(1):136-145 (2016).

De Oliveira et al. Neutrophil migration in infection and wound repair: going forward in reverse. Nat Rev Immunol 16:378-391 (2016).

Latourte et al. Prophylaxis for acute gout flares after initiation of urate-lowering therapy. Rheumatology 53(11):1920-1926 (2014).

Leung et al. Colchicine-Update on mechanisms of action and therapeutic uses. Seminars in Arthritis and Rheumatism 45(3):341-350 (2015).

Co-pending U.S. Appl. No. 16/601,294, filed Oct. 14, 2019.

Arend et al. IL-1, IL-18, and IL-33 families of cytokines. Immunol Rev 223:20-38 (2008).

Cao et al. Psoriasis and cardiovascular risk factors: increased serum myeloperoxidase and corresponding immunocellular overexpression by Cd11b(+) CD68(+) macrophages in skin lesions. Am J Transl Res 6(1):16-27 (2014).

Chemotaxis in Transwell Plates & CyQUANT Quantification. (1 pg.) (Edited Sep. 7, 2017).

Chou. Theoretical Basis, Experimental Design, and Computerized Simulation of Synergism and Antagonism in Drug Combination Studies, Pharmacol Rev 58:621-681 (2006).

Clarke. Issues in experimental design and endpoint analysis in the study of experimental cytotoxic agents in vivo in breast cancer and other models. Breast Cancer Res Treat 46:255-278 (1997).

Dinarello. Biologic basis for interleukin-1 in disease. Blood 87:2095-2147 (1996).

Elaraj et al. The role of interleukin 1 in growth and metastasis of human cancer xenografts. Clin Cancer Res 12:1088-1096 (2006).

Feldmeyer et al. Interleukin-1, inflammasomes and the skin. Eur J Cell Biol 89(9):638-644 (2010).

Gudjonsson et al. Mouse models of psoriasis. J Invest Dermatol 127(6):1292-1308 (2007).

Jensen. Targeting the IL-1 family members in skin inflammation. Curr Opin Investig Drugs 11(11):1211-1220 (2010).

Jin et al. Animal models of atopic dermatitis. J Invest Dermatol 129:31-40 (2009).

Kukle et al. The CXC receptor 2 is overexpressed in psoriatic epidermis. J Invest Dermatol 110:90-94 (1998).

Lewis et al. Interleukin-1 and cancer progression: the emerging role of interleukin-1 receptor antagonist as a novel therapeutic agent in cancer treatment. J Transl Med 4:48 (2006).

Lu et al. Inhibitory effect of colchicine on transforming growth factorl3l/Smads pathway in rat models of chronic pancreatitis. Zhongguo Zuzhi Gongcheng Yanjiu 18(49):8001-8006 (2014) (Chinese with English summary).

Malla et al. Effect of oral administration of AZD8309, a CXCR2 antagonist, on the severity of experimental pancreatitis. Pancreatology 16(5):761-769 (2016).

Nicholls et al. Myeloperoxidase and Cardiovascular Disease. Arterioscler Thromb Vasc Biol 25:1102-1111 (2005).

PCT/US2018/050656 International Search Report and Written Opinion dated Oct. 22, 2018.

Schon et al. Pathogenic function of IL-1 beta in psoriasiform skin lesions of flaky skin (fsn/fsn) mice. Clin Exp. Immunol 123:505-510 (2001).

Steele et al. CXCR2 inhibition suppresses acute and chronic pancreatic inflammation. Journal of Pathology 237:85-97 (Jun. 4, 2015).

U.S. Appl. No. 15/702,693 Office Action dated Apr. 15, 2019.

Voronov et al. IL-1 is required for tumor invasiveness and angiogenesis. PNAS USA100:2645-2650 (2003).

Wang et al. Roseotoxin B Improves Allergic Contact Dermatitis through a Unique Anti-Inflammatory Mechanism Involving Excessive Activation of Autophagy in Activated T Lymphocytes. J Invest Dermatol 136:1636-1646 (2016).

* cited by examiner

NEUTROPHILS

| IL-8-CM | − | + | − | − | − |
| MSU-CM | − | − | + | + | + |
| Cmpd 1 (10µM) | − | − | − | + | − |
| Cmpd 2 (10µM) | − | − | − | − | + |

PBMCs

| − | + | − | − | − |
| − | − | + | + | + |
| − | − | − | + | − |
| − | − | − | − | + |

CXCR-2 INHIBITORS FOR TREATING CRYSTAL ARTHROPATHY DISORDERS

CROSS-REFERENCE TO RELATED APPLICATIONS

This application is a U.S. National Stage entry of International Application No. PCT/US2017/021570, filed Mar. 9, 2017, which claims the benefit of U.S. Provisional Application Ser. No. 62/307,348, filed Mar. 11, 2016, all of which are hereby incorporated by reference in their entirety.

BACKGROUND OF THE INVENTION

Gout is associated with elevated levels of uric acid that crystallize and deposit in joints, tendons and surrounding tissues. Gout flares, often recurrent, are characterized by a sudden attack of excruciating joint pain, wherein the affected joint shows signs of tenderness, swelling, hotness, redness, and/or stiffness.

SUMMARY OF THE INVENTION

Provided herein are CXCR-2 inhibitor compounds and pharmaceutical compositions comprising said compounds. The subject compounds and compositions are useful for treating crystal arthropathy disorders, including gout, gouty arthritis and gout flares.

Some embodiments provided herein describe a method for treating a crystal arthropathy disease, the method comprising administering to a subject in need thereof a CXCR-2 inhibitor. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3), or a pharmaceutically acceptable salt thereof, or N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof.

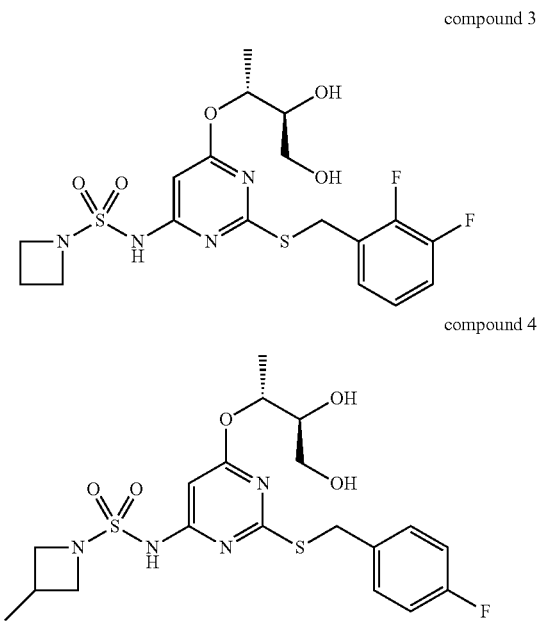

compound 3 compound 4

In some embodiments, the crystal arthropathy disease is monosodium urate crystal disease, uric acid crystal disease, calcium pyrophosphate disease, calcium crystal disease, basic calcium phosphate hydroxy-apatite deposition disease, calcific periarthritis disease, calcium oxalate aluminium phosphate deposition disease, xanthine deposition disease, Cysteine/cystine deposition disease, Charcot-Leyden disease, or lysophospho-lipase deposition disease.

Also provided herein in some embodiments is a method for treating a disease characterized by the accumulation of crystals in one or more joints, the method comprising administering to a subject in need thereof a CXCR-2 inhibitor. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3), or a pharmaceutically acceptable salt thereof, or N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof.

Other embodiments provided herein describe a method for treating a gout flare experienced by a subject, the method comprising administering to the subject a CXCR-2 inhibitor. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3), or a pharmaceutically acceptable salt thereof, or N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof.

Provided herein in some embodiments is a method for increasing the rapidity of relief of symptoms in a subject experiencing a gout flare or early symptoms of a gout flare, the method comprising administering to the subject a CXCR-2 inhibitor. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3), or a pharmaceutically acceptable salt thereof, or N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof.

Also provided herein is a method for reducing the duration or intensity of gout flares experienced by a subject, the method comprising administering to the subject a CXCR-2 inhibitor. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3), or a pharmaceutically acceptable salt thereof, or N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof.

In some embodiments, provided herein is a method of preventing or reducing the incidence of a gout flare, the method comprising administering to a subject in need thereof a CXCR-2 inhibitor. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3), or a pharmaceutically acceptable salt thereof, or N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof.

Other embodiments provided herein describe a method of preventing or reducing the incidence of a gout flare associated with gout therapy, the method comprising administering to a subject being treated for gout, a therapeutic amount of a CXCR-2 inhibitor. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3), or a pharmaceutically acceptable salt thereof, or N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof. In some embodiments, the gout therapy comprises treatment with a xanthine oxidase inhibitor, a URAT1 inhibitor, a uricosuric agent, a urate oxidase enzyme, PNP inhibitor, SGLT2 inhibitor or a combination thereof. In certain embodiments, the gout therapy is selected from allopurinol, febuxostat, uricase, pegylated uricase, rasburicase, probenecid, sulfinpyrazone, benzbromarone, fenofibrate, lesinurad, zurampic, Verinurad, arhalofenate, oral Bucillamine or combinations thereof.

Some embodiments provided herein describe a method for treating an acute gout flare, comprising concomitantly or sequentially administering to a subject in need thereof a combination of: (i) colchicine; and (ii) a CXCR-2 inhibitor. Also described herein in some embodiments is a method for preventing a gout flare, comprising concomitantly or sequentially administering to a subject in need thereof a combination of (i) colchicine; and (ii) a CXCR-2 inhibitor. Also provided herein in some embodiments is a method for the prophylaxis and treatment of gout flares in a subject, comprising concomitantly or sequentially administering to a subject in need thereof a combination of (i) colchicine; and (ii) a CXCR-2 inhibitor. In some embodiments, the subject is an adult. In further or additional embodiments, the combination is a synergistic combination. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3) or a pharmaceutically acceptable salt thereof, or N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof. In further or additional embodiments, the method comprises administering less than 1.2 mg of colchicine. In other embodiments, the method comprises administering less than 0.6 mg colchicine.

Also provided herein, in some embodiments, is a method for improving the therapeutic index of colchicine in a subject, the method comprising concomitantly or sequentially administering to the subject a CXCR-2 inhibitor.

Other embodiments provided herein describe a pharmaceutical composition comprising (i) colchicine; and (ii) a CXCR-2 inhibitor. In some embodiments, the pharmaceutical composition comprises (i) a therapeutically-effective amount of Colchicine; and (ii) a therapeutically-effective amount of a CXCR-2 inhibitor. In some embodiments, the pharmaceutical composition comprises (i) from about 0.1 mg to about 0.5 mg Colchicine; and (ii) a CXCR-2 inhibitor. In other embodiments, the pharmaceutical composition comprises (i) less than 0.5 mg Colchicine; and (ii) a CXCR-2 inhibitor. In some embodiments, the pharmaceutical composition further comprises a pharmaceutically acceptable diluent or carrier. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3) or a pharmaceutically acceptable salt thereof, or N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof.

Also described herein, in some embodiments, is a kit for treating a subject experiencing a gout flare, the kit comprising (i) a CXCR-2 inhibitor; and (ii) instructions for administration of the CXCR-2 inhibitor to treat the gout flare. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3) or a pharmaceutically acceptable salt thereof, or N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3) or a pharmaceutically acceptable salt thereof. In some embodiments, the CXCR-2 inhibitor is N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof. In further or additional embodiments, the kit comprises colchicine.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 depicts results of a cell migration assay with neutrophil and PBMC counts for compounds 1 and 2 (see Example 2).

FIG. 2 depicts the results from the rat air pouch model of crystal-induced arthropathy with compound 2 (see Example 4).

FIG. 3 depicts the results from the rat air pouch model of crystal-induced arthropathy with compound 2 in combination with colchicine (see Example 5).

FIG. 4 depicts the results from the rat air pouch model of crystal-induced arthropathy with compounds 2, 3, and 4 (see Example 6).

FIG. 5 depicts results from the rat air pouch model of crystal-induced arthropathy with compound 3 and compound 4 in combination with colchicine (see Example 7).

FIG. 6 depicts results from the rat air pouch model of crystal-induced arthropathy with compound 3 in combination with colchicine (see Example 8).

FIG. 7 depicts results from the rat air pouch model of crystal-induced arthropathy with compound 4 in combination with colchicine (see Example 9).

FIG. 8 depicts results from the rat air pouch model of crystal-induced arthropathy with compounds 3 and 4 in combination with colchicine (see Example 10).

DETAILED DESCRIPTION OF THE INVENTION

Definitions

Figure 1A:
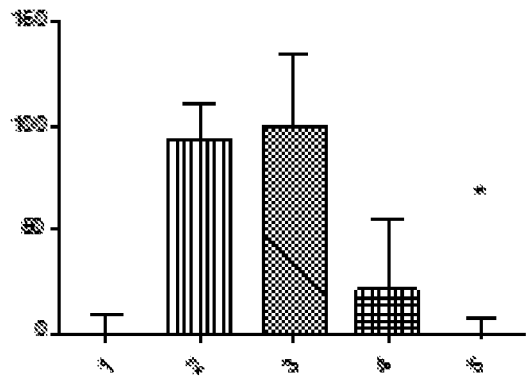
FIG. 1A depicts the Neutrophil counts.

The term "subject", as used herein in reference to individuals suffering from a disorder, and the like, encompasses mammals and non-mammals. In one embodiment of the methods and compositions provided herein, the mammal is a human.

The terms "effective amount", "therapeutically effective amount" or "pharmaceutically effective amount" as used herein, refer to an amount of at least one agent or compound being administered that is sufficient to treat or prevent the particular disease or condition. The result is the reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case is determined using techniques such as a dose escalation study.

A "sub-therapeutic amount" of an agent or therapy is an amount less than the effective amount for that agent or therapy, but when combined with an effective or sub-therapeutic amount of another agent or therapy can produce a result desired by the physician, due to, for example, synergy in the resulting efficacious effects, or reduced side effects.

A "synergistically effective" therapeutic amount of an agent or therapy is an amount which, when combined with an effective or sub-therapeutic amount of another agent or therapy, produces a greater effect than when either of the two agents are used alone. In some embodiments, a synergistically effective therapeutic amount of an agent or therapy produces a greater effect when used in combination than the additive effects of each of the two agents or therapies when used alone. The term "greater effect" encompasses not only a reduction in symptoms of the disorder to be treated, but also an improved side effect profile, improved tolerability, improved patient compliance, improved efficacy, or any other improved clinical outcome.

The terms "synergistic" and "synergistically" as applied to the effect of two or more pharmaceutically active ingredients used in combination (whether simultaneously or sequentially) refer to a greater effect than when either of the two agents are used alone.

The term "about" refers to +10% of a stated number or value.

In the context of the present specification, the term "therapy" also includes "prophylaxis" unless there are specific indications to the contrary. The terms "therapeutic" and "therapeutically" should be construed accordingly.

Agents

Colchicine

Colchicine is used to treat acute gout flares (and the symptoms associated therewith) as well as for prophylaxis of acute gout flares. While colchicine is neither an analgesic nor a uricosuric and will not prevent progression to chronic gouty arthritis, it does have a prophylactic, suppressive effect that helps to reduce the incidence of acute attacks and relieve residual pain.

Colchicine is rapidly absorbed from the gastrointestinal tract. Peak concentrations occur in 0.5 to 2 hours. The drug and its metabolites are distributed in leukocytes, kidneys, liver, spleen and the intestinal tract. Colchicine is metabolized in the liver and excreted primarily in the feces with 10-20% eliminated unchanged in the urine.

COLCRYS (colchicine, USP) is indicated for both the prophylaxis and treatment of gout flares (see for example the COLCRYS prescribing information or U.S. Pat. Nos. 7,964, 647 and 7,981,938). Prescribing information of COLCRYS requires:

0.6 mg once or twice daily to a maximum dose of 1.2 mg/day for prophylaxis of gout flares; and 1.2 mg at the first sign of a gout flare followed by 0.6 mg one hour later for treatment of gout flares.

Common side effects from taking COLCYS include diarrhea, nausea, vomiting, abdominal pain and pharyngolaryngeal pain. Warnings regarding the use of COLCRYS include blood dyscrasias (myelosuppression, leukopenia, granulocytopenia, thrombocytopenia and aplastic anemia); drug interaction with P-gp and/or CYP3A4 inhibitors (resulting in life-threatening interactions and death) and neuromuscular toxicity (myotoxicity including rhabdomyolysis).

The most frequently reported adverse side effects to colchicine therapy are gastrointestinal, specifically diarrhea; abdominal pain with cramps; nausea; and vomiting. Less frequently or rarely reported adverse side effects associated with colchicine therapy include anorexia, agranulocytosis, allergic dermatitis, allergic reactions, alopecia, angioedema, aplastic anemia, bone marrow depression, myopathy, neuropathy, skin rash, thrombocytopenic disorder and urticaria.

Clinical trial studies on colchicine (see U.S. Pat. No. 7,964,647) showed that a "standard" dose regimen of colchicine (1.2 mg administered at the onset of an acute gout attack followed by 0.6 mg every hour thereafter for 6 hours) resulted in more gastrointestinal side effects than placebo (73% vs. 19%) and more diarrhea than placebo (73% vs. 14%). Severe diarrhea occurred in 19% of patients and vomiting occurred in 15% of patients. A "lower" dose regimen (1.2 mg colchicine administered at the onset of an acute gout attack followed by 0.6 mg after one hour) resulted in more gastrointestinal side effects than placebo (24% vs. 19%) and more diarrhea than placebo (22% vs. 14%).

The "standard" dose of colchicine used to treat or prevent an attack of acute gouty arthritis was 1.0-1.2 mg, typically followed by 0.5-0.6 mg every hour, until pain is relieved or until diarrhea ensues ("diarrheal dose"). The dosing should be stopped if there is gastrointestinal discomfort or diarrhea. (Opiates may be needed to control diarrhea.) In subsequent attacks, the patient should be able to judge medication requirement accurately enough to stop short of the diarrheal dose. The total amount of colchicine needed to control pain and inflammation during an attack was believed to be in the 4-8 mg range. An interval of three days between colchicine courses was advised in order to minimize the possibility of cumulative toxicity.

CXCR-2 Inhibitors

Chemokines play an important role in immune and inflammatory responses in various diseases and disorders. These small secreted molecules are a growing superfamily of 8-14 kDa proteins characterized by a conserved cysteine motif.

The chemokine superfamily comprises three groups exhibiting characteristic structural motifs, the C—X—C, C—C and C—$X_3$—C families. The C—X—C chemokines include several potent chemo-attractants and activators of neutrophils such as interleukin-8 (IL-8) and neutrophil-activating peptide 2 (NAP-2).

Studies have demonstrated that the actions of the chemokines are mediated by subfamilies of G protein-coupled receptors, among which are the receptors designated CXCR-1, CXCR-2, CXCR-3, CXCR-4 and CXCR-5 (for the C—X—C family). Only IL-8, and certain other C—X—C chemokines that bind IL-8 receptors, are known to chemo-attract human neutrophils. Of the human C—X—C chemokine receptors identified to date (CXCR-1, 2, 3, 4 and 5), only CXCR-1 and CXCR-2 act as high-affinity IL-8 receptors. C—X—C chemokines that chemo-attract neutrophils share specific sequence motifs. These receptors represent good targets for drug development since agents that modulate these receptors would be useful in the treatment of immune and inflammatory related disorders and diseases.

CXCR-2 is an IL8 receptor. Chemokines that bind CXCR-2 are required for neutrophilic inflammation in acute gout (Terkaltaub et al, *Arthritis & Rheumatism*, (1988), Vol 41, (No 5) pp 900-909). Urate crystals can initiate, amplify and sustain an intense inflammatory attack because they stimulate the synthesis and release of humoral and cellular inflammatory mediators. Neutrophilic synovitis is the hallmark of an acute gouty attack. Neutrophils are rare in normal synovial fluid. Monosodium urate monohydrate (MSUM) crystals from supersaturated extracellular fluids are deposited in synovial tissue, which activates resident mononuclear phagocytes and synovial lining cells to release neutrophil chemotaxins—IL-8 and closely related, neutrophil chemotactic C—X—C chemokines. The newly generated neutrophil chemotaxins direct neutrophil transmigration. MSUM crystals interact with the phagocyte through two broad mechanisms. First, the crystals activate cells as opsonized and phagocytosed particles, eliciting the phagocyte response and release of inflammatory mediators. Second, urate crystals interact directly with lipid membranes and proteins, leading to the activation of several signal transduction pathways. These steps are critical for crystal-induced interleukin (IL)-8 expression. IL-8 is abundant in the synovial fluid in both acute gout and pseudogout. The rapid release of IL-8 (and other neutrophil chemotactic C—X—C chemokines) by crystal-activated resident mononuclear phagocytes and synovial lining cells triggers acute gout. Once in the synovial tissue, the neutrophils follow concentration gradients of chemoattractants such as C5a, leukotriene B4, platelet-activating factor, IL-1, and IL-8. Of these factors, IL-8 plays a central role in neutrophil invasion, accounting for approximately 90% of the neutrophil chemotactic activity of monocytes in response to urate crystals.

It has been postulated that colchicine's ability to suppress certain neutrophil responses to IL-8 could contribute to its' preventive and therapeutic properties in acute gout. Neutralization of IL-8 or its receptor CXCR-2 may substantially reduce the IL-8-induced neutrophilic inflammatory process and provide a potential therapeutic target in gout.

In some embodiments, the following compounds provided in the following table, or pharmaceutically acceptable salts thereof, may be useful to treat diseases in which the chemokine receptor belongs to the CXC chemokine receptor subfamily, more conveniently the target chemokine receptor is the CXCR-2 receptor. In some embodiments, the compounds 1, 2, 3, and 4 are CXCR-2 inhibitors.

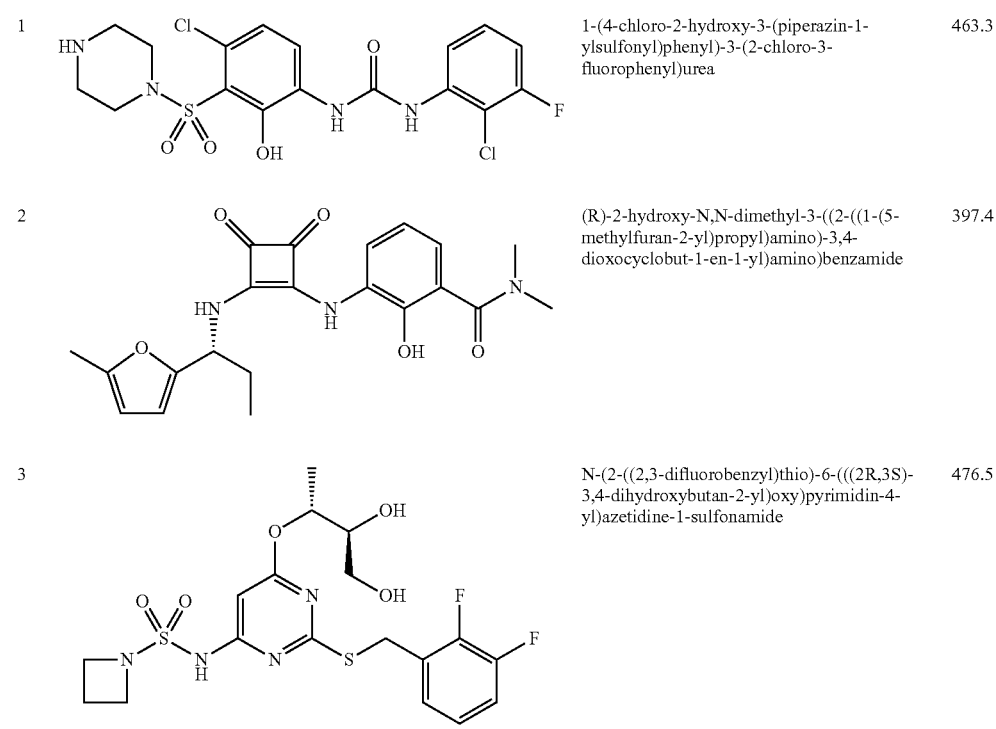

| | | | |
|---|---|---|---|
| 1 | | 1-(4-chloro-2-hydroxy-3-(piperazin-1-ylsulfonyl)phenyl)-3-(2-chloro-3-fluorophenyl)urea | 463.3 |
| 2 | | (R)-2-hydroxy-N,N-dimethyl-3-((2-((1-(5-methylfuran-2-yl)propyl)amino)-3,4-dioxocyclobut-1-en-1-yl)amino)benzamide | 397.4 |
| 3 | | N-(2-((2,3-difluorobenzyl)thio)-6-(((2R,3S)-3,4-dihydroxybutan-2-yl)oxy)pyrimidin-4-yl)azetidine-1-sulfonamide | 476.5 |

| | | |
|---|---|---|
| 4 | 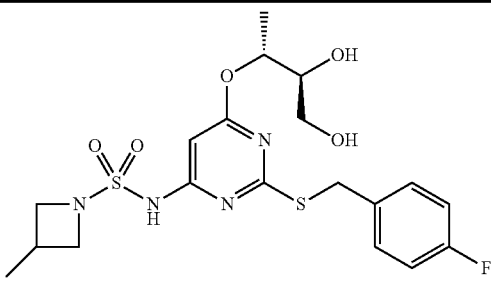 | N-(6-(((2R,3S)-3,4-dihydroxybutan-2-yl)oxy)-2-((4-fluorobenzyl)thio)pyrimidin-4-yl)-3-methylazetidine-1-sulfonamide  472.6 |

In some embodiments, compounds 1, 2, 3, and 4, or pharmaceutically acceptable salts thereof, are useful as pharmaceuticals, in particular as modulators of chemokine receptor (especially CXCR-2) activity, and may be used in the treatment (therapeutic or prophylactic) of conditions/diseases in human and non-human animals which are exacerbated or caused by excessive or unregulated production of chemokines. In particular embodiments, the condition/disease is gout flare. Thus, the present invention provides compounds 1, 2, 3 and 4, or pharmaceutically acceptable salts thereof, for use in therapy. In some embodiments, the present invention provides compounds 3 and 4, or pharmaceutically acceptable salts thereof, for use in therapy.

Compound 3 (N-(2-((2,3-difluorobenzyl)thio)-6-(((2R,3S)-3,4-dihydroxybutan-2-yl)oxy)pyrimidin-4-yl)azetidine-1-sulfonamide) and compound 4 (N-(6-(((2R,3S)-3,4-dihydroxy butan-2-yl)oxy)-2-((4-fluoro benzyl)thio)pyrimidin-4-yl)-3-methylazetidine-1-sulfonamide) are pyrimidinyl sulphonamides and are useful as modulators of chemokine receptors.

WO 2004/011443 describes pyrimidinyl sulphonamide derivatives for use as modulators of chemokine receptors.

The in vitro potency and PK parameters of compound 3 are described in WO 2006/024823 and WO 2010/007427. Compound 3 displays good bioavailability in rat (49%), a long half-life in dog, good solubility properties and high potency. Compound 3 was in Phase II trials for COPD. The preparation of compound 3, along with six crystalline forms, is described in WO 2012/007748.

The preparation of compound 4, along with several distinct crystalline forms, is described in WO 2013/008002.

Examples of other CXCR-2 inhibitors include but are not limited to, AZD-8309, AZ-10397767, elubrixin, danirixin, navarixin, reparixin, ladarixin, and meraxin. Additional examples of other CXCR-2 inhibitors include, but are not limited to, the compounds in the following table:

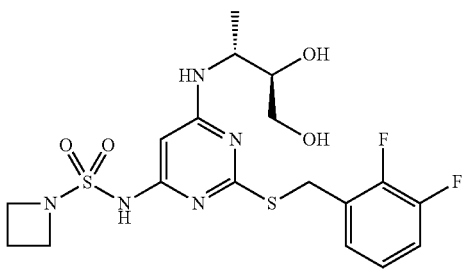 [SMILES: C[C@@H](Nc1cc(NS(=O)(=O)N2CCC2)nc(SCc2cccc(F)c2F)n1)[C@@H](O)CO]

N-(2-(2,3-difluorobenzylthio)-6-((2R,3R)-3,4-dihydroxybutan-2-ylamino)pyrimidin-4-yl)azetidine-1-sulfonamide

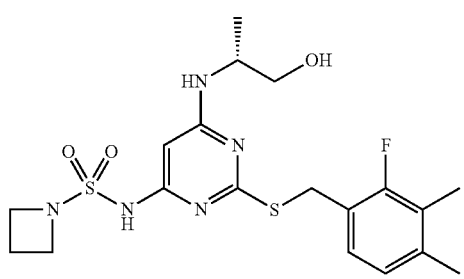 [SMILES: Cc1ccc(CSc2nc(N[C@H](C)CO)cc(NS(=O)(=O)N3CCC3)n2)c(F)c1C]

(R)-N-(2-(2-fluoro-3,4-dimethylbenzylthio)-6-(1-hydroxypropan-2-ylamino)pyrimidin-4-yl)azetidine-1-sulfonamide

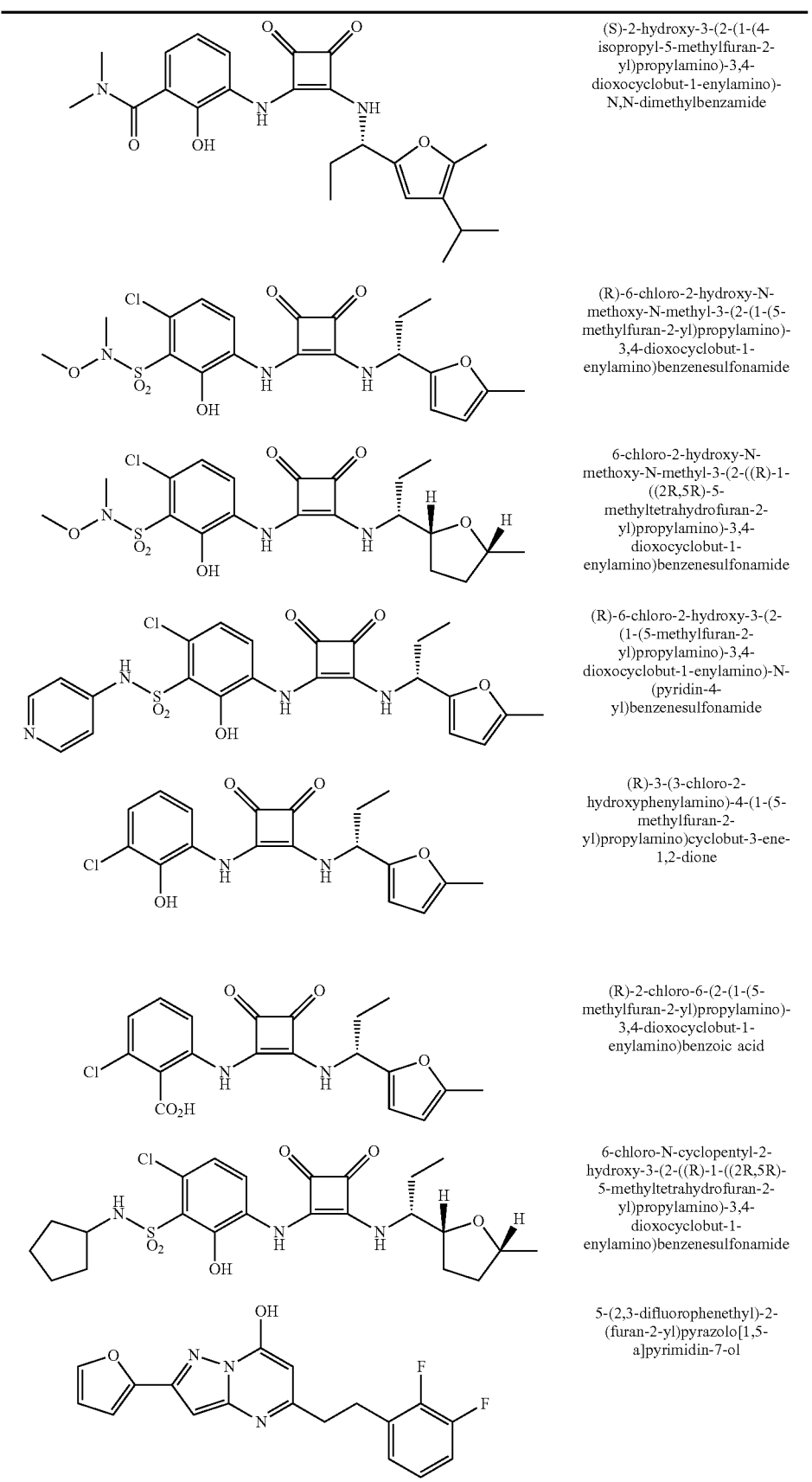

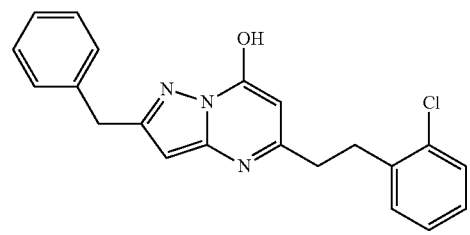 [SMILES: Oc1cc(CCc2ccccc2Cl)nc2cc(Cc3ccccc3)nn12]

2-benzyl-5-(2-chlorophenethyl)pyrazolo[1,5-a]pyrimidin-7-ol

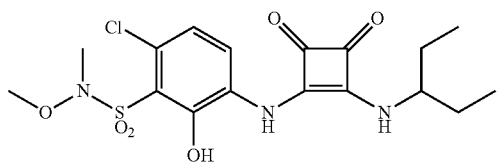 [SMILES: CCC(CC)Nc1c(Nc2ccc(Cl)c(S(=O)(=O)N(C)OC)c2O)c(=O)c1=O]

6-chloro-3-(3,4-dioxo-2-(pentan-3-ylamino)cyclobut-1-enylamino)-2-hydroxy-N-methoxy-N-methylbenzenesulfonamide

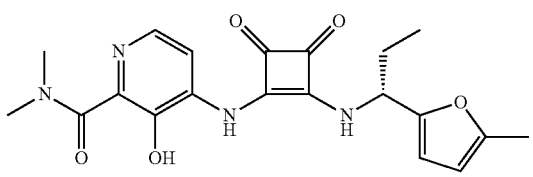

(R)-3-hydroxy-N,N-dimethyl-4-(2-(1-(5-methylfuran-2-yl)propylamino)-3,4-dioxocyclobut-1-enylamino)picolinamide

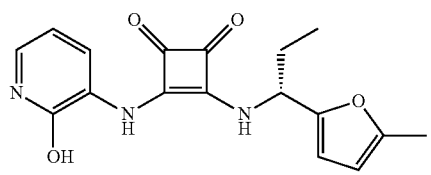 [SMILES: CC[C@@H](Nc1c(Nc2cccnc2O)c(=O)c1=O)c1ccc(C)o1]

(R)-3-(2-hydroxypyridin-3-ylamino)-4-(1-(5-methylfuran-2-yl)propylamino)cyclobut-3-ene-1,2-dione

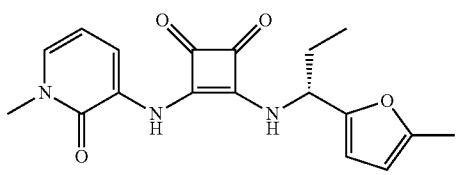

(R)-3-(1-methyl-2-oxo-1,2-dihydropyridin-3-ylamino)-4-(1-(5-methylfuran-2-yl)propylamino)cyclobut-3-ene-1,2-dione

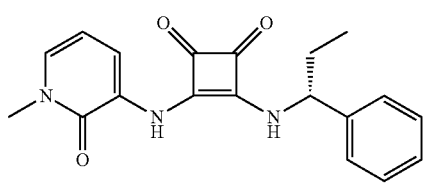 [SMILES: CC[C@@H](Nc1c(Nc2cccn(C)c2=O)c(=O)c1=O)c1ccccc1]

(R)-3-(1-methyl-2-oxo-1,2-dihydropyridin-3-ylamino)-4-(1-phenylpropylamino)cyclobut-3-ene-1,2-dione

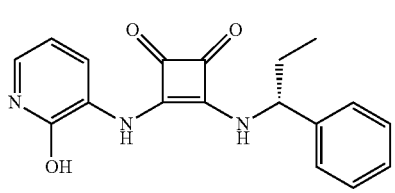 [SMILES: CC[C@@H](Nc1c(Nc2cccnc2O)c(=O)c1=O)c1ccccc1]

(R)-3-(2-hydroxypyridin-3-ylamino)-4-(1-phenylpropylamino)cyclobut-3-ene-1,2-dione

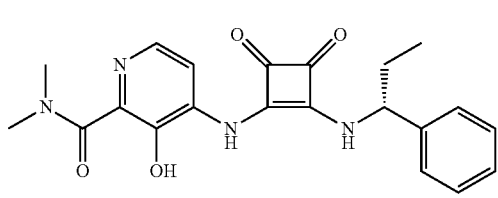 [SMILES: CC[C@@H](Nc1c(Nc2ccnc(C(=O)N(C)C)c2O)c(=O)c1=O)c1ccccc1]

(R)-4-(3,4-dioxo-2-(1-phenylpropylamino)cyclobut-1-enylamino)-3-hydroxy-N,N-dimethylpicolinamide

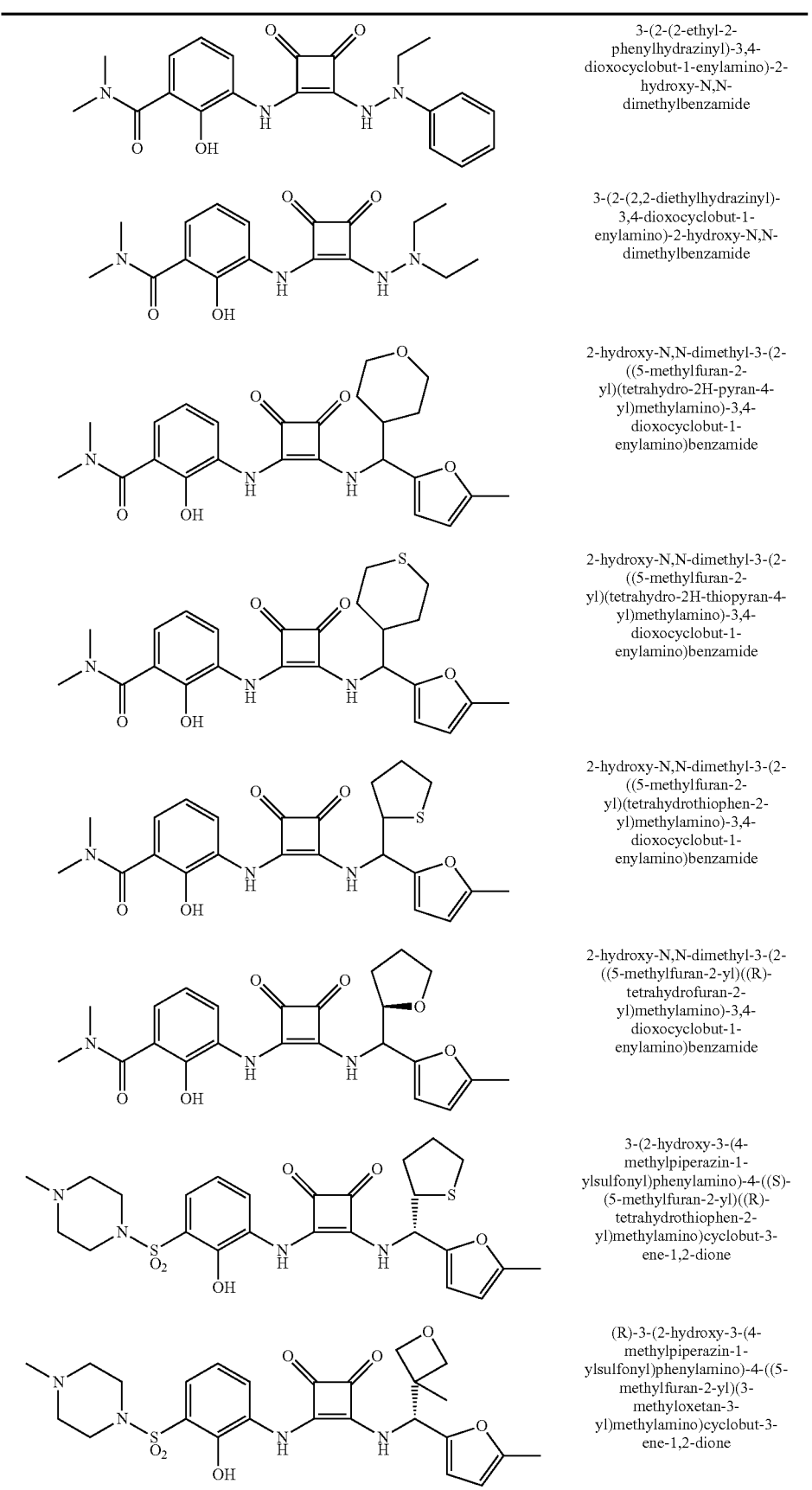

| | |
|---|---|
| | 3-(2-(2-ethyl-2-phenylhydrazinyl)-3,4-dioxocyclobut-1-enylamino)-2-hydroxy-N,N-dimethylbenzamide |
| | 3-(2-(2,2-diethylhydrazinyl)-3,4-dioxocyclobut-1-enylamino)-2-hydroxy-N,N-dimethylbenzamide |
| | 2-hydroxy-N,N-dimethyl-3-(2-((5-methylfuran-2-yl)(tetrahydro-2H-pyran-4-yl)methylamino)-3,4-dioxocyclobut-1-enylamino)benzamide |
| | 2-hydroxy-N,N-dimethyl-3-(2-((5-methylfuran-2-yl)(tetrahydro-2H-thiopyran-4-yl)methylamino)-3,4-dioxocyclobut-1-enylamino)benzamide |
| | 2-hydroxy-N,N-dimethyl-3-(2-((5-methylfuran-2-yl)(tetrahydrothiophen-2-yl)methylamino)-3,4-dioxocyclobut-1-enylamino)benzamide |
| | 2-hydroxy-N,N-dimethyl-3-(2-((5-methylfuran-2-yl)((R)-tetrahydrofuran-2-yl)methylamino)-3,4-dioxocyclobut-1-enylamino)benzamide |
| | 3-(2-hydroxy-3-(4-methylpiperazin-1-ylsulfonyl)phenylamino)-4-((S)-(5-methylfuran-2-yl)((R)-tetrahydrothiophen-2-yl)methylamino)cyclobut-3-ene-1,2-dione |
| | (R)-3-(2-hydroxy-3-(4-methylpiperazin-1-ylsulfonyl)phenylamino)-4-((5-methylfuran-2-yl)(3-methyloxetan-3-yl)methylamino)cyclobut-3-ene-1,2-dione |

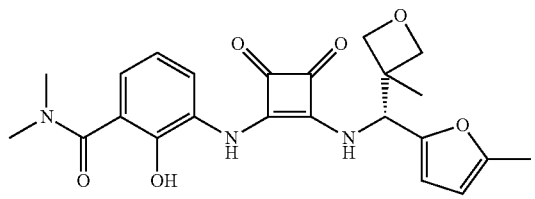

(R)-2-hydroxy-N,N-dimethyl-3-(2-((5-methylfuran-2-yl)(3-methyloxetan-3-yl)methylamino)-3,4-dioxocyclobut-1-enylamino)benzamide

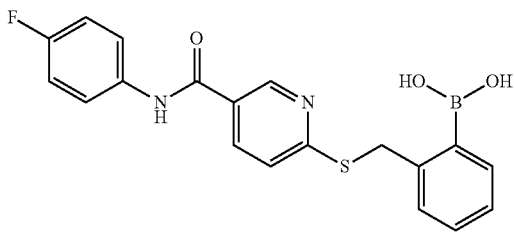 [SMILES: O=C(Nc1ccc(F)cc1)c1ccc(SCc2ccccc2B(O)O)nc1]

2-((5-(4-fluorophenylcarbamoyl)pyridin-2-ylthio)methyl)phenylboronic acid

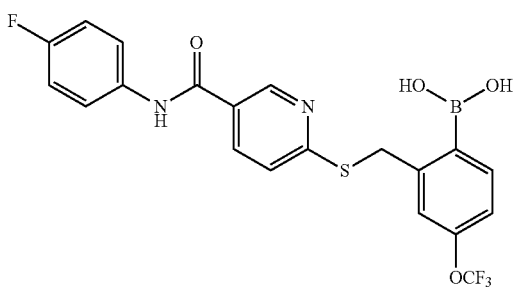

2-((5-(4-fluorophenylcarbamoyl)pyridin-2-ylthio)methyl)-4-(trifluoromethoxy)phenylboronic acid

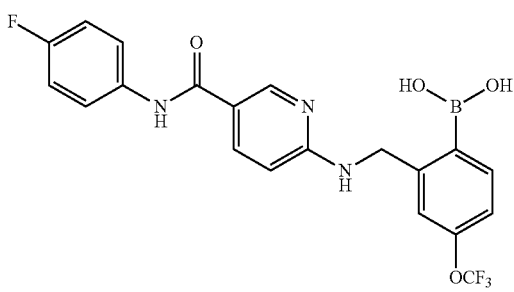 [SMILES: O=C(Nc1ccc(F)cc1)c1ccc(NCc2cc(OC(F)(F)F)ccc2B(O)O)nc1]

2-((5-(4-fluorophenylcarbamoyl)pyridin-2-ylamino)methyl)-4-(trifluoromethoxy)phenylboronic acid

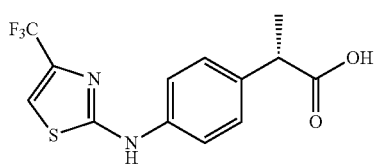 [SMILES: C[C@H](C(=O)O)c1ccc(Nc2nc(C(F)(F)F)cs2)cc1]

(S)-2-(4-(4-(trifluoromethyl)thiazol-2-ylamino)phenyl)propanoic acid

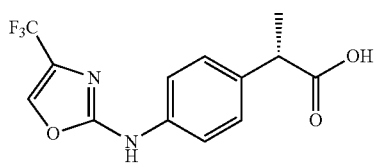 [SMILES: C[C@H](C(=O)O)c1ccc(Nc2nc(C(F)(F)F)co2)cc1]

(S)-2-(4-(4-(trifluoromethyl)oxazol-2-ylamino)phenyl)propanoic acid

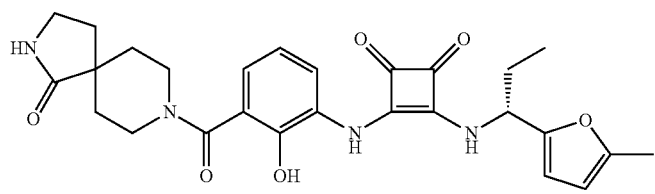 [SMILES: CC[C@@H](Nc1c(Nc2cccc(C(=O)N3CCC4(CCNC4=O)CC3)c2O)c(=O)c1=O)c1ccc(C)o1]

(R)-3-(2-hydroxy-3-(1-oxo-2,8-diazaspiro[4.5]decane-8-carbonyl)phenylamino)-4-(1-(5-methylfuran-2-yl)propylamino)cyclobut-3-ene-1,2-dione

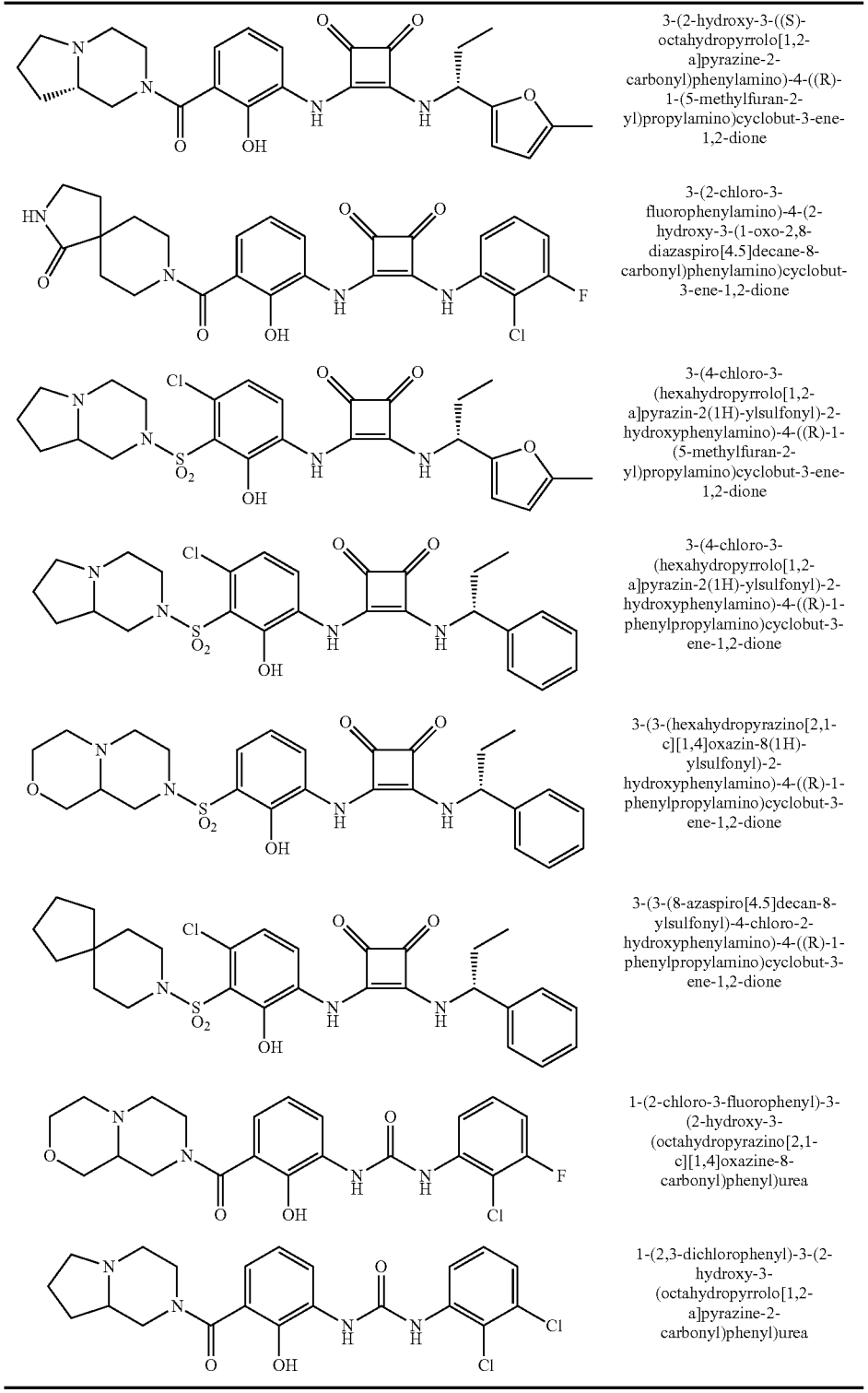

| | |
|---|---|
| | 3-(2-hydroxy-3-((S)-octahydropyrrolo[1,2-a]pyrazine-2-carbonyl)phenylamino)-4-((R)-1-(5-methylfuran-2-yl)propylamino)cyclobut-3-ene-1,2-dione |
| | 3-(2-chloro-3-fluorophenylamino)-4-(2-hydroxy-3-(1-oxo-2,8-diazaspiro[4.5]decane-8-carbonyl)phenylamino)cyclobut-3-ene-1,2-dione |
| | 3-(4-chloro-3-(hexahydropyrrolo[1,2-a]pyrazin-2(1H)-ylsulfonyl)-2-hydroxyphenylamino)-4-((R)-1-(5-methylfuran-2-yl)propylamino)cyclobut-3-ene-1,2-dione |
| | 3-(4-chloro-3-(hexahydropyrrolo[1,2-a]pyrazin-2(1H)-ylsulfonyl)-2-hydroxyphenylamino)-4-((R)-1-phenylpropylamino)cyclobut-3-ene-1,2-dione |
| | 3-(3-(hexahydropyrazino[2,1-c][1,4]oxazin-8(1H)-ylsulfonyl)-2-hydroxyphenylamino)-4-((R)-1-phenylpropylamino)cyclobut-3-ene-1,2-dione |
| | 3-(3-(8-azaspiro[4.5]decan-8-ylsulfonyl)-4-chloro-2-hydroxyphenylamino)-4-((R)-1-phenylpropylamino)cyclobut-3-ene-1,2-dione |
| | 1-(2-chloro-3-fluorophenyl)-3-(2-hydroxy-3-(octahydropyrazino[2,1-c][1,4]oxazine-8-carbonyl)phenyl)urea |
| | 1-(2,3-dichlorophenyl)-3-(2-hydroxy-3-(octahydropyrrolo[1,2-a]pyrazine-2-carbonyl)phenyl)urea |

In a still further aspect, the present invention provides the use of compounds 1, 2, 3 and 4, or pharmaceutically acceptable salts thereof, as hereinbefore defined, for use as a medicament for the treatment of crystal arthropathy disease, gout, gouty arthritis and gout flare.

In a further aspect, the present invention provides the use of compounds 1, 2, 3 and 4, or pharmaceutically acceptable salts thereof, as hereinbefore defined in the manufacture of a medicament for use in therapy.

In a still further aspect, the present invention provides the use of compounds 1, 2, 3 and 4, or pharmaceutically acceptable salts thereof, as hereinbefore defined in the manufacture of a medicament for the treatment of human diseases or conditions in which modulation of chemokine receptor activity is beneficial.

In a still further aspect, the present invention provides the use of compounds 1, 2, 3 and 4, or pharmaceutically acceptable salts thereof, as hereinbefore defined in the manufacture of a medicament for the treatment of crystal arthropathy disease, gout, gouty arthritis and gout flare.

Methods

Described herein is a method of treating crystal arthopathy disease, gout, gouty arthritis or gout flare, in a patient suffering from, or at risk of, said disease, which comprises administering to the patient a therapeutically effective amount of a CXCR-2 inhibitor, or a pharmaceutically acceptable salt thereof. In some embodiments, the CXCR-2 inhibitor is compound 1, 2, 3 or 4, or pharmaceutically acceptable salts thereof. In some embodiments, the CXCR-2 inhibitor is compound 3 or 4, or pharmaceutically acceptable salts thereof. In some embodiments, the CXCR-2 inhibitor is compound 3 or pharmaceutically acceptable salts thereof. In some embodiments, the CXCR-2 inhibitor is compound 4 or pharmaceutically acceptable salts thereof.

Crystal Arthropathy Disease

Crystal arthropathy is a class of joint disorder (arthropathy) characterized by accumulation of tiny crystals in one or more joints. Polarizing microscopy allows identification of different microcrystals including monosodium urate, calcium-pyrophosphate (chondrocalcinosis or pseudogout), calcium hydroxyapatite, and calcium oxalate. Risk factors for developing crystal arthropathy include obesity, renal failure, hyperphosphatemia, hyperparathyroidism, hypercalcemia and tissue damage (dystrophic calcification).

Provided herein are methods for treating a crystal arthropathy disease by administering to a subject in need thereof a CXCR-2 inhibitor. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3), or a pharmaceutically acceptable salt thereof, or N-(6-(((2R,3S)-3,4-dihydroxy butan-2-yl)oxy)-2-((4-fluoro benzyl)thio)pyrimidin-4-yl)-3-methylazetidine-1-sulfonamide (compound 4) or a pharmaceutically acceptable salt thereof. In some embodiments, the methods for treating a crystal arthropathy disease comprise administering to a subject in need thereof N-(2-((2,3-difluorobenzyl)thio)-6-(((2R,3S)-3,4-dihydroxybutan-2-yl)oxy)pyrimidin-4-yl)azetidine-1-sulfonamide (compound 3), or a pharmaceutically acceptable salt thereof. In some embodiments, the methods for treating a crystal arthropathy disease comprise administering to a subject in need thereof N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof.

Also described herein are methods for treating a crystal arthropathy disease by administering to a subject in need thereof 1-(4-chloro-2-hydroxy-3-(piperazin-1-ylsulfonyl)phenyl)-3-(2-chloro-3-fluorophenyl)urea (compound 1), or a pharmaceutically acceptable salt thereof, or (R)-2-hydroxy-N,N-dimethyl-3-((2-((1-(5-methylfuran-2-yl)propyl)amino)-3,4-dioxocyclobut-1-en-1-yl)amino)benzamide (compound 2), or a pharmaceutically acceptable salt thereof.

In some embodiments, the crystal arthropathy disease is monosodium urate crystal disease, uric acid crystal disease, calcium pyrophosphate disease, calcium crystal disease, basic calcium phosphate hydroxy-apatite deposition disease, calcific periarthritis disease, calcium oxalate aluminium phosphate deposition disease, xanthine deposition disease, Cysteine/cystine deposition disease, Charcot-Leyden disease, or lysophospho-lipase deposition disease. In some embodiments, the crystal arthropathy disease is monosodium urate crystal disease. In some embodiments, the crystal arthropathy disease is uric acid crystal disease. In some embodiments, the crystal arthropathy disease is calcium pyrophosphate disease. In some embodiments, the crystal arthropathy disease is calcium crystal disease. In some embodiments, the crystal arthropathy disease is basic calcium phosphate hydroxy-apatite deposition disease. In some embodiments, the crystal arthropathy disease is calcific periarthritis disease. In some embodiments, the crystal arthropathy disease is calcium oxalate aluminium phosphate deposition disease. In some embodiments, the crystal arthropathy disease is xanthine deposition disease. In some embodiments, the crystal arthropathy disease is Cysteine/cystine deposition disease. In some embodiments, the crystal arthropathy disease is Charcot-Leyden disease. In some embodiments, the crystal arthropathy disease is lysophospho-lipase deposition disease.

Disease Characterized by Accumulation of Crystals

Also described herein are methods for treating a disease characterized by the accumulation of crystals in one or more joints by administering to a subject in need thereof a CXCR-2 inhibitor. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3) or a pharmaceutically acceptable salt thereof, or N-(6-(((2R,3S)-3,4-dihydroxy butan-2-yl)oxy)-2-((4-fluoro benzyl)thio)pyrimidin-4-yl)-3-methylazetidine-1-sulfonamide (compound 4) or a pharmaceutically acceptable salt thereof. In some embodiments, the methods for treating a disease characterized by the accumulation of crystals in one or more joints comprises administering to a subject in need thereof a CXCR-2 inhibitor. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3), or a pharmaceutically acceptable salt thereof. In some embodiments, the methods for treating a disease characterized by the accumulation of crystals in one or more joints comprise administering to a subject in need thereof N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof.

Also described herein are methods for treating a disease characterized by the accumulation of crystals in one or more joints by administering to a subject in need thereof 1-(4-chloro-2-hydroxy-3-(piperazin-1-ylsulfonyl)phenyl)-3-(2-chloro-3-fluorophenyl)urea (compound 1), or a pharmaceutically acceptable salt thereof; or (R)-2-hydroxy-N,N-dimethyl-3-((2-((1-(5-methylfuran-2-yl)propyl)amino)-3,4-dioxocyclobut-1-en-1-yl)amino)benzamide (compound 2), or a pharmaceutically acceptable salt thereof.

Gout

Gout is a disease caused by buildup of uric acid (due to either an overproduction of uric acid or, more commonly, a reduced ability of the kidney to excrete uric acid) leading to crystal deposition in joints and the surrounding tissues, provoking an inflammatory response. Acute gouty arthritis (or a "gout flare" or a "gout attack") is a sudden attack of pain, frequently starting during the night, and usually involves only one or a few joints; the big toe, knee, or ankle joints are most often affected. The pain has been described as throbbing, crushing, burning or excruciating. The affected joint may show signs of warmth or hotness, redness, tenderness, swelling and/or stiffness. Low-grade fever may also be present. The crystals inside the joint cause intense pain whenever the affected area is moved. Inflammation of the tissues surrounding the affected joint may cause the skin to swell, and become tender and sore to even the slightest pressure.

Chronic gout involves repeated attacks of joint pain, which often last longer. Several gout attacks within a year, can lead to joint deformity and limited motion in joints. Uric acid deposits, called tophi, develop in cartilage tissue, tendons, and soft tissues, though usually develop only after a patient has suffered from the disease for many years. Deposits also can occur in the kidneys, leading to chronic kidney failure.

Gout Flares

Also described herein are methods for treating a gout flare experienced by a subject by administering to a subject in need thereof a CXCR-2 inhibitor. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3) or a pharmaceutically acceptable salt thereof, or N-(6-(((2R,3S)-3,4-dihydroxy butan-2-yl)oxy)-2-((4-fluoro benzyl)thio)pyrimidin-4-yl)-3-methylazetidine-1-sulfonamide (compound 4) or a pharmaceutically acceptable salt thereof. In some embodiments, the methods for treating a gout flare experienced by a subject comprise administering to a subject in need thereof N-(2-((2,3-difluorobenzyl)thio)-6-(((2R,3S)-3,4-dihydroxybutan-2-yl)oxy)pyrimidin-4-yl)azetidine-1-sulfonamide (compound 3), or a pharmaceutically acceptable salt thereof. In some embodiments, the methods for treating a gout flare experienced by a subject comprise administering to a subject in need thereof N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof.

Also described herein are methods for treating a gout flare experienced by a subject by administering to a subject in need thereof 1-(4-chloro-2-hydroxy-3-(piperazin-1-ylsulfonyl)phenyl)-3-(2-chloro-3-fluorophenyl)urea (compound 1), or a pharmaceutically acceptable salt thereof; or (R)-2-hydroxy-N,N-dimethyl-3-((2-((1-(5-methylfuran-2-yl)propyl)amino)-3,4-dioxocyclobut-1-en-1-yl)amino)benzamide (compound 2), or a pharmaceutically acceptable salt thereof.

Also described herein are methods for increasing the rapidity of relief of symptoms in a subject experiencing a gout flare or early symptoms of a gout flare by administering to a subject in need thereof a CXCR-2 inhibitor. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3) or a pharmaceutically acceptable salt thereof, or N-(6-(((2R,3S)-3,4-dihydroxy butan-2-yl)oxy)-2-((4-fluoro benzyl)thio)pyrimidin-4-yl)-3-methylazetidine-1-sulfonamide (compound 4) or a pharmaceutically acceptable salt thereof. In some embodiments, the methods for increasing the rapidity of relief of symptoms in a subject experiencing a gout flare or early symptoms of a gout flare comprise administering to a subject in need thereof N-(2-((2,3-difluorobenzyl)thio)-6-(((2R,3S)-3,4-dihydroxybutan-2-yl)oxy)pyrimidin-4-yl)azetidine-1-sulfonamide (compound 3), or a pharmaceutically acceptable salt thereof. In some embodiments, the methods for increasing the rapidity of relief of symptoms in a subject experiencing a gout flare or early symptoms of a gout flare comprise administering to a subject in need thereof N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof.

Also described herein are methods for increasing the rapidity of relief of symptoms in a subject experiencing a gout flare or early symptoms of a gout flare by administering to a subject in need thereof 1-(4-chloro-2-hydroxy-3-(piperazin-1-ylsulfonyl)phenyl)-3-(2-chloro-3-fluorophenyl)urea (compound 1), or a pharmaceutically acceptable salt thereof; or (R)-2-hydroxy-N,N-dimethyl-3-((2-((1-(5-methylfuran-2-yl)propyl)amino)-3,4-dioxocyclobut-1-en-1-yl)amino)benzamide (compound 2), or a pharmaceutically acceptable salt thereof.

Also described herein are methods for reducing the duration or intensity of gout flares experienced by a subject by administering to a subject in need thereof a CXCR-2 inhibitor. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3) or a pharmaceutically acceptable salt thereof, or N-(6-(((2R,3S)-3,4-dihydroxy butan-2-yl)oxy)-2-((4-fluoro benzyl)thio)pyrimidin-4-yl)-3-methylazetidine-1-sulfonamide (compound 4) or a pharmaceutically acceptable salt thereof. In some embodiments, the methods for reducing the duration or intensity of gout flares experienced by a subject comprise administering to a subject in need thereof N-(2-((2,3-difluorobenzyl)thio)-6-(((2R,3S)-3,4-dihydroxybutan-2-yl)oxy)pyrimidin-4-yl)azetidine-1-sulfonamide (compound 3), or a pharmaceutically acceptable salt thereof. In some embodiments, the methods for reducing the duration or intensity of gout flares experienced by a subject comprise administering to a subject in need thereof N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof.

Also described herein are methods for reducing the duration or intensity of gout flares experienced by a subject by administering to a subject in need thereof 1-(4-chloro-2-hydroxy-3-(piperazin-1-ylsulfonyl)phenyl)-3-(2-chloro-3-fluorophenyl)urea (compound 1), or a pharmaceutically acceptable salt thereof; or (R)-2-hydroxy-N,N-dimethyl-3-((2-((1-(5-methylfuran-2-yl)propyl)amino)-3,4-dioxocyclobut-1-en-1-yl)amino)benzamide (compound 2), or a pharmaceutically acceptable salt thereof.

Also described herein are methods of preventing or reducing the incidence of a gout flare by administering to a subject in need thereof a CXCR-2 inhibitor. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3) or a pharmaceutically acceptable salt thereof, or N-(6-(((2R,3S)-3,4-dihydroxy butan-2-yl)oxy)-2-((4-fluoro benzyl)thio)pyrimidin-4-yl)-3-methylazetidine-1-sulfonamide (compound 4) or a pharmaceutically acceptable salt thereof. In some embodiments, the methods of preventing or reducing the incidence of a gout flare comprise administering to a subject in need thereof N-(2-((2,3-difluorobenzyl)thio)-6-(((2R,3S)-3,4-dihydroxybutan-2-yl)oxy)pyrimidin-4-yl)azetidine-1-sulfonamide (compound 3), or a pharmaceutically acceptable salt thereof. In some embodiments, the methods of preventing or reducing the incidence of a gout flare comprise administering to a subject in need thereof N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof.

Also described herein are methods preventing or reducing the incidence of a gout flare by administering to a subject in need thereof 1-(4-chloro-2-hydroxy-3-(piperazin-1-ylsulfonyl)phenyl)-3-(2-chloro-3-fluorophenyl)urea (compound 1), or a pharmaceutically acceptable salt thereof; or (R)-2-hydroxy-N,N-dimethyl-3-((2-((1-(5-methylfuran-2-yl)propyl)amino)-3,4-dioxocyclobut-1-en-1-yl)amino)benzamide (compound 2), or a pharmaceutically acceptable salt thereof.

In some instances, an increase in gout flares occurs after initiation of gout therapy (e.g., uric acid-lowering therapy) due to changing serum uric acid levels resulting in mobilization of urate from tissue deposits. In some instances, prophylactic therapy is beneficial for the first 6 months of uric acid-lowering therapy. Described herein are methods of preventing or reducing the incidence of a gout flare associated with gout therapy by administering to a subject in need thereof a CXCR-2 inhibitor. In some embodiments, the CXCR-2 inhibitor is N-(2-((2,3-difluorobenzyl)thio)-6-(((2R,3S)-3,4-dihydroxybutan-2-yl)oxy)pyrimidin-4-yl) azetidine-1-sulfonamide (compound 3) or a pharmaceutically acceptable salt thereof, or N-(6-(((2R,3S)-3,4-dihydroxy butan-2-yl)oxy)-2-((4-fluoro benzyl)thio) pyrimidin-4-yl)-3-methylazetidine-1-sulfonamide (compound 4) or a pharmaceutically acceptable salt thereof. In some embodiments, the methods of preventing or reducing the incidence of a gout flare associated with gout therapy comprise administering to a subject in need thereof N-(2-((2,3-difluorobenzyl)thio)-6-(((2R,3S)-3,4-dihydroxybutan-2-yl)oxy)pyrimidin-4-yl)azetidine-1-sulfonamide (compound 3), or a pharmaceutically acceptable salt thereof. In some embodiments, the methods of preventing or reducing the incidence of a gout flare associated with gout therapy comprise administering to a subject in need thereof N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof. In some embodiments, the gout therapy comprises treatment with a xanthine oxidase inhibitor, a URAT1 inhibitor, a uricosuric agent, a urate oxidase enzyme, PNP inhibitor, SGLT2 inhibitor or a combination thereof. In some embodiments, the gout therapy is selected from allopurinol, febuxostat, uricase, pegylated uricase, rasburicase, probenecid, sulfinpyrazone, benzbromarone, fenofibrate, lesinurad, zurampic, Verinurad, rhalofenate, oral Bucillamine or combinations thereof.

In some embodiments, the CXCR-2 inhibitor is administered prophylactically for the first 1, 2, 3, 4, 5, 6, 7, 8, 9, 10, 11, or 12 months of uric acid-lowering therapy. In some embodiments, the CXCR-2 inhibitor is administered prophylactically for the first 6 months of uric acid-lowering therapy. In some embodiments, the CXCR-2 inhibitor is administered prophylactically for the first 3-6 months of uric acid-lowering therapy. In some embodiments, the CXCR-2 inhibitor is administered prophylactically for the first 6-9 months of uric acid-lowering therapy. In some embodiments, the CXCR-2 inhibitor is administered prophylactically for the first 9-12 months of uric acid-lowering therapy. In some embodiments, the CXCR-2 inhibitor is administered prophylactically for the first 3-9 months of uric acid-lowering therapy.

Also described herein are methods preventing or reducing the incidence of a gout flare associated with gout therapy by administering to a subject in need thereof 1-(4-chloro-2-hydroxy-3-(piperazin-1-ylsulfonyl)phenyl)-3-(2-chloro-3-fluorophenyl)urea (compound 1), or a pharmaceutically acceptable salt thereof; or (R)-2-hydroxy-N,N-dimethyl-3-((2-((1-(5-methylfuran-2-yl)propyl)amino)-3,4-dioxocyclobut-1-en-1-yl)amino)benzamide (compound 2), or a pharmaceutically acceptable salt thereof. In some embodiments, the gout therapy comprises treatment with a xanthine oxidase inhibitor, a URAT1 inhibitor, a uricosuric agent, a urate oxidase enzyme, PNP inhibitor, SGLT2 inhibitor or a combination thereof. In some embodiments, the gout therapy is selected from allopurinol, febuxostat, uricase, pegylated uricase, rasburicase, probenecid, sulfinpyrazone, benzbromarone, fenofibrate, lesinurad, zurampic, Verinurad, arhalofenate, oral Bucillamine or combinations thereof.

Combinations with Colchicine

Also described herein are combination therapies wherein any one of the CXCR-2 inhibitors disclosed herein, or pharmaceutically acceptable salts thereof, is administered concurrently or sequentially with an additional therapy and/or an agent for the treatment of crystal arthropathy disease, gout, gouty arthritis or gout flare. In some embodiments, a CXCR-2 inhibitor, or pharmaceutically acceptable salt thereof, is administered concurrently or sequentially with an additional an agent for the treatment of gout, gouty arthritis or gout flare. In some embodiments, the CXCR-2 inhibitor, or pharmaceutically acceptable salts thereof, is administered concurrently or sequentially with colchicine. In some embodiments, the CXCR-2 inhibitor is compound 1, 2, 3, or 4, or the pharmaceutically acceptable salt thereof.

Also described herein are methods for treating an acute gout flare by concomitantly or sequentially administering to a subject in need thereof a combination of (i) Colchicine; and (ii) a CXCR-2 inhibitor. In some embodiments, the combination is a synergistic combination. In some embodiments, the CXCR-2 inhibitor is one of the compounds disclosed herein, or a pharmaceutically acceptable salt thereof. In some embodiments, the CXCR-2 inhibitor is 1-(4-chloro-2-hydroxy-3-(piperazin-1-ylsulfonyl)phenyl)-3-(2-chloro-3-fluorophenyl)urea (compound 1), or a pharmaceutically acceptable salt thereof. In some embodiments, the CXCR-2 inhibitor is (R)-2-hydroxy-N,N-dimethyl-3-((2-((1-(5-methylfuran-2-yl)propyl)amino)-3,4-dioxocyclobut-1-en-1-yl)amino)benzamide (compound 2), or a pharmaceutically acceptable salt thereof. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3) or a pharmaceutically acceptable salt thereof. In some embodiments, the CXCR-2 inhibitor is N-(6-(((2R,3S)-3,4-dihydroxy butan-2-yl)oxy)-2-((4-fluoro benzyl)thio)pyrimidin-4-yl)-3-methylazetidine-1-sulfonamide (compound 4) or a pharmaceutically acceptable salt thereof.

In some embodiments, the methods comprise administering less than 1.2 mg colchicine. In some embodiments, the methods comprise administering less than 0.6 mg colchicine. In some embodiments, the methods comprise administering less than 1.2 mg, 1.1 mg, 1.0 mg, 0.9 mg, 0.8 mg, 0.7 mg, 0.6 mg, 0.5 mg, 0.4 mg, 0.3 mg, 0.2 mg, or 0.1 mg colchicine. In some embodiments, the methods comprise administering about 1.2 mg, about 1.1 mg, about 1.0 mg, about 0.9 mg, about 0.8 mg, about 0.7 mg, about 0.6 mg, about 0.5 mg, about 0.4 mg, about 0.3 mg, about 0.2 mg, or about 0.1 mg colchicine. In some embodiments, the methods comprise administering about 0.05 to 0.55 mg colchicine. In some embodiments, the methods comprise administering about 0.2 to 0.4 mg colchicine. In some embodiments, the methods comprise administering about 0.1 to 0.3 mg colchicine.

Also described herein are methods for preventing a gout flare by concomitantly or sequentially administering to a subject in need thereof a combination of (i) Colchicine; and (ii) a CXCR-2 inhibitor. In some embodiments, the combination is a synergistic combination. In some embodiments, the CXCR-2 inhibitor is one of the compounds disclosed herein, or a pharmaceutically acceptable salt thereof. In some embodiments, the CXCR-2 inhibitor is 1-(4-chloro-2-hydroxy-3-(piperazin-1-ylsulfonyl)phenyl)-3-(2-chloro-3-fluorophenyl)urea (compound 1), or a pharmaceutically acceptable salt thereof. In some embodiments, the CXCR-2 inhibitor is (R)-2-hydroxy-N,N-dimethyl-3-((2-((1-(5-methylfuran-2-yl)propyl)amino)-3,4-dioxocyclobut-1-en-1-yl)amino)benzamide (compound 2), or a pharmaceutically acceptable salt thereof. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3) or a pharmaceutically acceptable salt thereof. In some embodiments, the CXCR-2 inhibitor is N-(6-(((2R,3S)-3,4-dihydroxy butan-2-yl)oxy)-2-((4-fluoro benzyl)thio)pyrimidin-4-yl)-3-methylazetidine-1-sulfonamide (compound 4) or a pharmaceutically acceptable salt thereof.

In some embodiments, the methods comprise administering less than 1.2 mg colchicine. In some embodiments, the methods comprise administering less than 0.6 mg colchicine. In some embodiments, the methods comprise administering less than 1.2 mg, 1.1 mg, 1.0 mg, 0.9 mg, 0.8 mg, 0.7 mg, 0.6 mg, 0.5 mg, 0.4 mg, 0.3 mg, 0.2 mg, or 0.1 mg colchicine. In some embodiments, the methods comprise administering about 1.2 mg, about 1.1 mg, about 1.0 mg, about 0.9 mg, about 0.8 mg, about 0.7 mg, about 0.6 mg, about 0.5 mg, about 0.4 mg, about 0.3 mg, about 0.2 mg, or about 0.1 mg colchicine. In some embodiments, the methods comprise administering about 0.05 to 0.55 mg colchicine. In some embodiments, the methods comprise administering about 0.2 to 0.4 mg colchicine. In some embodiments, the methods comprise administering about 0.1 to 0.3 mg colchicine.

Also described herein are methods for improving the therapeutic index of colchicine in a subject by concomitantly or sequentially administering to a subject in need thereof a combination of (i) Colchicine; and (ii) a CXCR-2 inhibitor. In some embodiments, the combination is a synergistic combination. In some embodiments, the CXCR-2 inhibitor is one of the compounds disclosed herein, or a pharmaceutically acceptable salt thereof. In some embodiments, the CXCR-2 inhibitor is 1-(4-chloro-2-hydroxy-3-(piperazin-1-ylsulfonyl)phenyl)-3-(2-chloro-3-fluorophenyl)urea (compound 1), or a pharmaceutically acceptable salt thereof. In some embodiments, the CXCR-2 inhibitor is (R)-2-hydroxy-N,N-dimethyl-3-((2-((1-(5-methylfuran-2-yl)propyl)amino)-3,4-dioxocyclobut-1-en-1-yl)amino)benzamide (compound 2), or a pharmaceutically acceptable salt thereof. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3) or a pharmaceutically acceptable salt thereof. In some embodiments, the CXCR-2 inhibitor is N-(6-(((2R,3S)-3,4-dihydroxy butan-2-yl)oxy)-2-((4-fluoro benzyl)thio)pyrimidin-4-yl)-3-methylazetidine-1-sulfonamide (compound 4) or a pharmaceutically acceptable salt thereof.

In some embodiments, the methods comprise administering less than 1.2 mg colchicine. In some embodiments, the methods comprise administering less than 0.6 mg colchicine. In some embodiments, the methods comprise administering less than 1.2 mg, 1.1 mg, 1.0 mg, 0.9 mg, 0.8 mg, 0.7 mg, 0.6 mg, 0.5 mg, 0.4 mg, 0.3 mg, 0.2 mg, or 0.1 mg colchicine. In some embodiments, the methods comprise administering about 1.2 mg, about 1.1 mg, about 1.0 mg, about 0.9 mg, about 0.8 mg, about 0.7 mg, about 0.6 mg, about 0.5 mg, about 0.4 mg, about 0.3 mg, about 0.2 mg, or about 0.1 mg colchicine. In some embodiments, the methods comprise administering about 0.05 to 0.55 mg colchicine. In some embodiments, the methods comprise administering about 0.2 to 0.4 mg colchicine. In some embodiments, the methods comprise administering about 0.1 to 0.3 mg colchicine.

Also described herein are methods for the prophylaxis and treatment of gout flares in a subject by concomitantly or sequentially administering to a subject in need thereof a combination of (i) Colchicine; and (ii) a CXCR-2 inhibitor. In some embodiments, the subject is an adult. In some embodiments, the combination is a synergistic combination. In some embodiments, the CXCR-2 inhibitor is one of the compounds disclosed herein, or a pharmaceutically acceptable salt thereof. In some embodiments, the CXCR-2 inhibitor is 1-(4-chloro-2-hydroxy-3-(piperazin-1-ylsulfonyl)phenyl)-3-(2-chloro-3-fluorophenyl)urea (compound 1), or a pharmaceutically acceptable salt thereof. In some embodiments, the CXCR-2 inhibitor is (R)-2-hydroxy-N,N-dimethyl-3-((2-((1-(5-methylfuran-2-yl)propyl)amino)-3,4-dioxocyclobut-1-en-1-yl)amino)benzamide (compound 2), or a pharmaceutically acceptable salt thereof. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3) or a pharmaceutically acceptable salt thereof. In some embodiments, the CXCR-2 inhibitor is N-(6-(((2R,3S)-3,4-dihydroxy butan-2-yl)oxy)-2-((4-fluoro benzyl)thio)pyrimidin-4-yl)-3-methylazetidine-1-sulfonamide (compound 4) or a pharmaceutically acceptable salt thereof.

In some embodiments, the methods comprise administering less than 1.2 mg colchicine. In some embodiments, the methods comprise administering less than 0.6 mg colchicine. In some embodiments, the methods comprise administering less than 1.2 mg, 1.1 mg, 1.0 mg, 0.9 mg, 0.8 mg, 0.7 mg, 0.6 mg, 0.5 mg, 0.4 mg, 0.3 mg, 0.2 mg, or 0.1 mg colchicine. In some embodiments, the methods comprise administering about 1.2 mg, about 1.1 mg, about 1.0 mg, about 0.9 mg, about 0.8 mg, about 0.7 mg, about 0.6 mg, about 0.5 mg, about 0.4 mg, about 0.3 mg, about 0.2 mg, or about 0.1 mg colchicine. In some embodiments, the methods comprise administering about 0.05 to 0.55 mg colchicine. In some embodiments, the methods comprise administering about 0.2 to 0.4 mg colchicine. In some embodiments, the methods comprise administering about 0.1 to 0.3 mg colchicine.

In some embodiments, administration of a combination of colchicine and a CXCR-2 inhibitor provides a synergistic effect. As used herein, the terms "synergy," "synergistically," "synergistic" or other grammatical equivalents thereof mean an interaction of two or more compounds such that the effect is additive (i.e., the effect of the two compounds is greater than either individually) or that the addition of one compound results in less of the other compound being required. In some embodiments, the co-administration of the CXCR-2 inhibitor, such as compound 3 or compound 4, or pharmaceutically acceptable salts thereof, results in the need for a smaller dose of a second active agent. In some embodiments, the co-administration of a second active agent and the CXCR-2 inhibitor, such as compound 3 or compound 4, or pharmaceutically acceptable salts thereof results in the need for a smaller dose of the CXCR-2 inhibitor, such as compound 3 or compound 4, or pharmaceutically acceptable salts thereof. In some embodiments, the co-administration of the CXCR-2 inhibitor, such as compound 3 or compound 4, or pharmaceutically acceptable salts thereof, results in the need for a smaller dose of colchicine to treat or prevent a gout flare. In some embodiments, the smaller dose of colchicine and/CXCR-2 inhibitor is a sub-therapeutically effective amount.

It is difficult to predict the effect of many combination therapies. For example, some drugs interact with each other to reduce therapeutic effectiveness or cause undesired side-effects. These drugs are typically categorized as having an antagonistic effect. Other drug combinations manifest their therapeutic effectiveness as the sum of individual drugs. These combinations are categorized as having an additive effect. Still other drug combinations result in a therapeutic index that is greater than the sum of individual drugs. These are categorized as having a synergistic effect.

Combination therapies having a synergistic effect are highly desirable for many reasons. For example, each component in the synergistic combination therapy can be used in an amount lower than the therapeutic amount of each individual drug in monotherapy (i.e., single drug administration). Moreover, the risk and/or the severity of side-effects can be reduced significantly by reducing the amount of each drug. Furthermore, combination therapy may significantly increase the overall effectiveness of treatment.

Synergistic actions of combination therapy are particularly useful in treatments where the side-effects are extreme or severe and/or where the efficacy of monotherapy is less than desirable. Therapeutic synergy represents a therapeutic effect achieved with a tolerated regimen of a combination treatment that exceeds the optimal effect achieved at any tolerated dose of monotherapy associated with the same drugs used in the combination.

Pharmaceutical Compositions

The compound, compound forms and compositions described herein are administered either alone, or in combination with, pharmaceutically acceptable adjuvants, carriers, excipients, or diluents in a pharmaceutical composition, according to standard pharmaceutical practice.

Described herein in some embodiments are pharmaceutical compositions comprising a CXCR-2 inhibitor, such as any one of the compounds described herein, or the pharmaceutically acceptable salt thereof in association with a pharmaceutically acceptable adjuvant, diluent or carrier. In some embodiments, the CXCR-2 inhibitor is 1-(4-chloro-2-hydroxy-3-(piperazin-1-ylsulfonyl)phenyl)-3-(2-chloro-3-fluorophenyl)urea (compound 1), or a pharmaceutically acceptable salt thereof. In some embodiments, the CXCR-2 inhibitor is (R)-2-hydroxy-N,N-dimethyl-3-((2-((1-(5-methylfuran-2-yl)propyl)amino)-3,4-dioxocyclobut-1-en-1-yl)amino)benzamide (compound 2), or a pharmaceutically acceptable salt thereof. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3) or a pharmaceutically acceptable salt thereof. In some embodiments, the CXCR-2 inhibitor is N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof. In some embodiments, the pharmaceutical compositions further comprise colchicine.

Also described herein in some embodiments are pharmaceutical compositions comprising colchicine and a CXCR-2 inhibitor in association with a pharmaceutically acceptable adjuvant, diluent or carrier. Also disclosed herein are pharmaceutical compositions comprising a therapeutically-effective amount of Colchicine, and a therapeutically-effective amount of a CXCR-2 inhibitor. Also disclosed herein are pharmaceutical compositions comprising a sub-therapeutically-effective amount of Colchicine, and a sub-therapeutically-effective amount of a CXCR-2 inhibitor. In some embodiments, the pharmaceutical compositions have a fixed dose combination. In some embodiments, the pharmaceutical compositions comprise from about 0.1 mg to about 0.5 mg Colchicine; and a CXCR-2 inhibitor. In some embodiments, the pharmaceutical compositions comprise about 0.1 mg, about 0.2 mg, about 0.3 mg, about 0.4 mg, or about 0.5 mg Colchicine; and a CXCR-2 inhibitor. In some embodiments, the pharmaceutical compositions comprise from about 0.1 mg to about 0.6 mg Colchicine; and a CXCR-2 inhibitor. In some embodiments, the pharmaceutical compositions comprise about 0.1 mg, about 0.2 mg, about 0.3 mg, about 0.4 mg, about 0.5 mg, or about 0.6 mg Colchicine; and a CXCR-2 inhibitor. In some embodiments, the pharmaceutical compositions comprise from about 0.1 mg to about 1.0 mg Colchicine; and a CXCR-2 inhibitor. In some embodiments, the pharmaceutical compositions comprise about 0.1 mg, about 0.2 mg, about 0.3 mg, about 0.4 mg, about 0.5 mg, about 0.6 mg, about 0.7 mg, about 0.8 mg, about 0.9 mg, or 1.0 mg Colchicine; and a CXCR-2 inhibitor. In some embodiments, the pharmaceutical compositions comprise less than 0.5 mg of Colchicine; and a CXCR-2 inhibitor. In some embodiments, the pharmaceutical compositions further comprise a pharmaceutically acceptable diluent or carrier.

In some embodiments, the CXCR-2 inhibitor is one of the compounds disclosed herein, or a pharmaceutically acceptable salt thereof. In some embodiments, the CXCR-2 inhibitor is 1-(4-chloro-2-hydroxy-3-(piperazin-1-ylsulfonyl)phenyl)-3-(2-chloro-3-fluorophenyl)urea (compound 1), or a pharmaceutically acceptable salt thereof. In some embodiments, the CXCR-2 inhibitor is (R)-2-hydroxy-N,N-dimethyl-3-((2-((1-(5-methylfuran-2-yl)propyl)amino)-3,4-dioxocyclobut-1-en-1-yl)amino)benzamide (compound 2), or a pharmaceutically acceptable salt thereof. In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3) or a pharmaceutically acceptable salt thereof. In some embodiments, the CXCR-2 inhibitor is N-(6-(((2R,3S)-3,4-dihydroxy butan-2-yl)oxy)-2-((4-fluoro benzyl)thio)pyrimidin-4-yl)-3-methylazetidine-1-sulfonamide (compound 4) or a pharmaceutically acceptable salt thereof.

In some embodiments, the pharmaceutical compositions are for the treatment of disorders. In some embodiments, the pharmaceutical compositions are for the treatment of disorders in a mammal. In some embodiments, the pharmaceutical compositions are for the treatment of disorders in a human. In some embodiments, the pharmaceutical compositions are for the treatment or prophylaxis of crystal arthropathy diseases. In some embodiments, the pharmaceutical compositions are for the treatment or prophylaxis of diseases characterized by the accumulation of crystals in one or more joints. In some embodiments, the pharmaceutical compositions are for the treatment or prophylaxis of gout, gouty arthritis, and gout flares.

Depending on the mode of administration, the pharmaceutical composition will conveniently comprise from 0.05 to 99% w (percent by weight), more conveniently from 0.05 to 80% w, still more conveniently from 0.10 to 70% w, and even more conveniently from 0.10 to 50% w, of active ingredient, all percentages by weight being based on total composition.

Also described herein are processes for the preparation of a pharmaceutical composition of the invention which comprise mixing a CXCR-2 inhibitor (e.g., compound 3 or 4), or pharmaceutically acceptable salts thereof, with a pharmaceutically acceptable adjuvant, diluent or carrier. In some embodiments, the pharmaceutical compositions are administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Conveniently, compound 3 or compound 4, or pharmaceutically acceptable salts thereof, is administered orally.

Modes of Administration

The compound, compound forms and compositions described herein are administered either alone, or in combination with, pharmaceutically acceptable adjuvants, carriers, excipients, or diluents in a pharmaceutical composition, according to standard pharmaceutical practice.

The pharmaceutical compositions described herein are, for example, in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition is, in some embodiments, in unit dosage forms suitable for single administration of precise dosages. Pharmaceutical compositions include a compound or compound form as described herein as an active ingredient, and a conventional pharmaceutical carrier or excipient. In some embodiments, these compositions include other or additional medicinal or pharmaceutical agents, carriers, adjuvants, etc.

Pharmaceutical compositions are conveniently presented in unit dosage form. In some embodiments, they are prepared with a specific amount of active compound by any of the methods well known or apparent to those skilled in the pharmaceutical arts.

Doses

The amount of pharmaceutical compositions administered will firstly be dependent on the mammal being treated. In the instances where pharmaceutical compositions are administered to a human subject, the daily dosage will normally be determined by the prescribing physician with the dosage generally varying according to the age, sex, diet, weight, general health and response of the individual patient, the severity of the patient's symptoms, the precise indication or condition being treated, the severity of the indication or condition being treated, time of administration, route of administration, the disposition of the composition, rate of excretion, drug combination, and the discretion of the prescribing physician. Also, the route of administration varies depending on the condition and its severity. The pharmaceutical composition is, in some embodiments, in unit dosage form. In such form, the preparation is subdivided into unit doses containing appropriate quantities of the active component, e.g., an effective amount to achieve the desired purpose. Determination of the proper dosage for a particular situation is within the skill of the art. For convenience, in some embodiments, the total daily dosage is divided and administered in portions during the day if desired. The amount and frequency of administration will be regulated according to the judgment of the attending clinician physician considering such factors as described above. Thus, the amount of pharmaceutical composition to be administered is variable depending upon the circumstances. In some instances, dosage levels below the lower limit of the aforesaid range are more than adequate, while in other cases still larger doses are employed without causing any harmful side effect, e.g. by dividing such larger doses into several small doses for administration throughout the day. In combinational applications in which the compound is not the sole therapy, it is possible to administer lesser amounts of compound and still have therapeutic or prophylactic effect.

Kits

The compounds, compound forms, compositions and methods described herein provide kits for the treatment of diseases and disorders, such as the ones described herein. These kits comprise a compound, compound form, compounds, compound forms or compositions described herein in a container and, optionally, instructions teaching the use of the kit according to the various methods and approaches described herein. Such kits, in some embodiments, also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein are provided, marketed and/or promoted to health providers, including physicians, nurses, pharmacists, formulary officials, and the like. Kits are also, in some embodiments, marketed directly to the consumer.

Described herein are compositions or kits comprising a CXCR-2 inhibitor, such as any one of the compounds described herein, or the pharmaceutically acceptable salt thereof.

In some embodiments, the CXCR-2 inhibitor is N-(2-((2,3-difluorobenzyl)thio)-6-(((2R,3S)-3,4-dihydroxybutan-2-yl)oxy)pyrimidin-4-yl)azetidine-1-sulfonamide (compound 3) or a pharmaceutically acceptable salt thereof. In some embodiments, the CXCR-2 inhibitor is N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof. In some embodiments, the kits further comprise Colchicine.

Described herein are compositions or kits for treating a subject experiencing a gout flare comprising a CXCR-2 inhibitor, such as any one of the compounds described herein, and instructions for administration of the CXCR-2 inhibitor to treat the gout flare. In some embodiments, the CXCR-2 inhibitor is N-(2-((2,3-difluorobenzyl)thio)-6-(((2R,3S)-3,4-dihydroxybutan-2-yl)oxy)pyrimidin-4-yl) azetidine-1-sulfonamide (compound 3) or a pharmaceutically acceptable salt thereof. In some embodiments, the CXCR-2 inhibitor is N-(6-(((2R,3S)-3,4-dihydroxy butan-2-yl)oxy)-2-((4-fluoro benzyl)thio)pyrimidin-4-yl)-3-methylazetidine-1-sulfonamide (compound 4), or a pharmaceutically acceptable salt thereof. In some embodiments, the kits further comprise Colchicine.

Provided in certain embodiments, are compositions or kits comprising a CXCR-2 inhibitor, a double low density polyethylene plastic bag, and an HDPE container. In further embodiments, the composition or kit further comprises a foil bag (e.g., an anhydrous foil bag, such as a heat sealed anhydrous foil bag). In some embodiments, the composition or kit further comprises a desiccant; in still other embodiments, a desiccant is not necessary and/or present. In some instances, such packing improves the stability of the CXCR-2 inhibitor.

In some embodiments, the compounds, compound forms and pharmaceutical compositions described herein are utilized for diagnostics and as research reagents. For example, in some embodiments, the compounds, compound forms and pharmaceutical compositions, either alone or in combination with other compounds, are used as tools in differential and/or combinatorial analyses to elucidate expression patterns of genes expressed within cells and tissues. As one non-limiting example, expression patterns within cells or tissues treated with one or more compounds are compared to control cells or tissues not treated with compounds and the patterns produced are analyzed for differential levels of gene expression as they pertain, for example, to disease association, signaling pathway, cellular localization, expression level, size, structure or function of the genes examined. These analyses are performed on stimulated or unstimulated cells and in the presence or absence of other compounds which affect expression patterns.

Besides being useful for human treatment, the compounds, compound forms and pharmaceutical compositions described herein are also useful for veterinary treatment of animals.

The examples and preparations provided below further illustrate and exemplify the compounds of the present invention and methods of preparing such compounds. It is to be understood that the scope of the present invention is not limited in any way by the scope of the following examples and preparations.

EXAMPLES

The following examples further illustrate the invention but should not be construed as in any way limiting its scope. In particular, the processing conditions are merely exemplary and can be readily varied by one of ordinary skill in the art.

All methods described herein can be performed in a suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. Unless defined otherwise, technical and scientific terms used herein have the same meaning as is commonly understood by one of skill in the art to which this invention belongs.

Embodiments of this invention are described herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited herein. Moreover, any combination of the above-described elements in all possible variations thereof is encompassed by the invention unless otherwise indicated herein or otherwise clearly contradicted by context.

Example 1: Test Compounds

Compounds 1, 2, 3 and 4, alone or in combination with colchicine, were tested in disease models of crystal-induced arthropathy.

| No. | Structure | Chemical Name | MW |
|---|---|---|---|
| 1 | 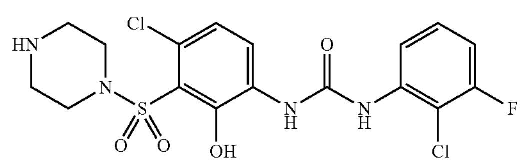 [SMILES: O=C(Nc1ccc(Cl)c(S(=O)(=O)N2CCNCC2)c1O)Nc1cccc(F)c1Cl] | 1-(4-chloro-2-hydroxy-3-(piperazin-1-ylsulfonyl)phenyl)-3-(2-chloro-3-fluorophenyl)urea | 463.3 |
| 2 | 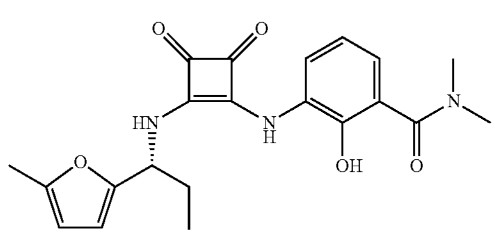 | (R)-2-hydroxy-N,N-dimethyl-3-((2-((1-(5-methylfuran-2-yl)propyl)amino)-3,4-dioxocyclobut-1-en-1-yl)amino)benzamide | 397.4 |
| 3 | 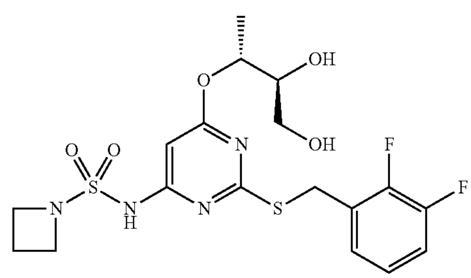 [SMILES: C[C@@H](Oc1cc(NS(=O)(=O)N2CCC2)nc(SCc2cccc(F)c2F)n1)[C@@H](O)CO] | N-(2-((2,3-difluorobenzyl)thio)-6-(((2R,3S)-3,4-dihydroxybutan-2-yl)oxy)pyrimidin-4-yl)azetidine-1-sulfonamide | 476.5 |

| No. | Structure | Chemical Name | MW |
|---|---|---|---|
| 4 | 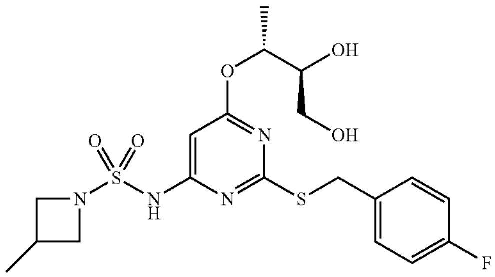 [SMILES: CC1CN(S(=O)(=O)Nc2cc(O[C@H](C)[C@@H](O)CO)nc(SCc3ccc(F)cc3)n2)C1] | N-(6-(((2R,3S)-3,4-dihydroxybutan-2-yl)oxy)-2-((4-fluoro benzyl)thio)pyrimidin-4-yl)-3-methylazetidine-1-sulfonamide | 472.6 |
| | | COLCHICINE | 399.4 |

Colchicine was obtained from Sigma Aldrich. Compounds 1, 2, 3, and 4 were shown to inhibit CXCR-2 (see Dwyer & Yu, *Expert Opin. Ther. Patents* (2014), 24(5), 519). Compound 1 has been described previously (see for example WO 2009/039091) and was obtained from R&D Systems. Compound 2 was previously described (see for example WO 2009/073683) and was obtained from Medchem Express. Compound 3 was previously described and was prepared as shown in U.S. Pat. No. 8,748,603. Compound 4 was prepared as shown in Scheme 1 (below) and in U.S. Pat. No. 8,735,413.

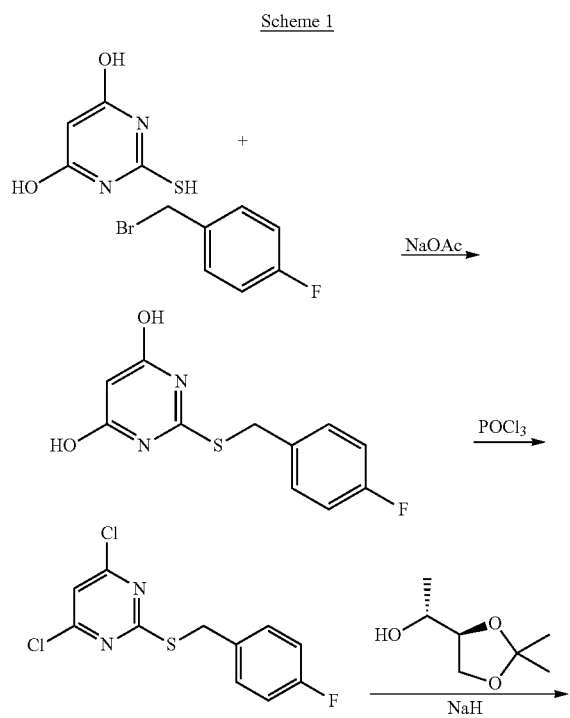

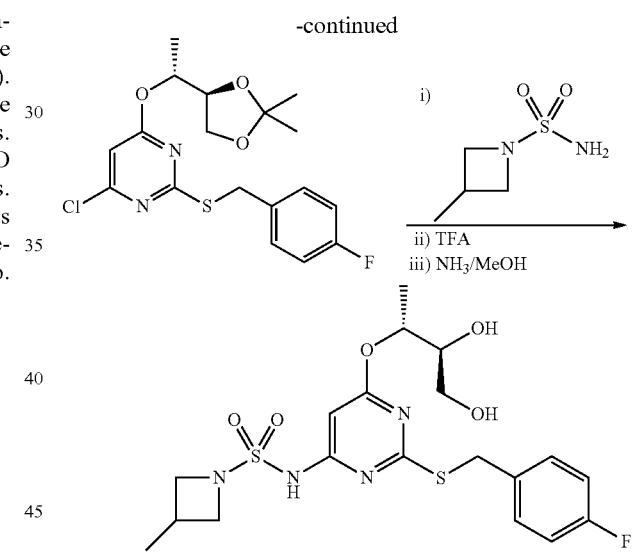

Example 2: Cell Migration Assay (In Vitro Inflammation)

Example 2A: Monocyte Isolation from Leukopacks

Primary blood monocytes (PMBC) were obtained from the lymphocyte layer (buffy coat) of peripheral blood from normal donors. Each leukopack (Interstate Blood Bank) was diluted with an equal volume of PBS, and 35 mL of blood preparation was over-laid onto 15 mL of Ficoll-Paque™ PLUS (GE Healthcare Bio-Sciences). Tubes were centrifuged at 700×g without breaks for 30 minutes at room temperature.

The buffy coat interface was removed, added to PBS (40 mL), and centrifuged at 300×g. Any remaining erythrocytes in the cell pellet were lysed by incubating cells in red blood cell lysis buffer (10 mL, R&D Systems) for 10 minutes at room temperature. Following lysis, PBS (40 mL) was added and the cells centrifuged for 5 minutes at 200×g. The pellet was washed once with PBS and re-suspended in complete RPMI and seeded onto a BD Falcon™ 100 mm tissue culture dish (Cat. No. 353003). After one hour, the media was aspirated and the adherent cells (predominantly monocytes) were harvested using a cell scraper and used in chemotaxis assays.

Example 2B: Chemotaxis Assay

Chemotaxis was assayed in 48-well plates with BD Falcon FluoroBlok Multiwell inserts with 3 μm pores (Cat. No. 351161 or 351162) coated with hFN. Briefly, freshly isolated monocytes were re-suspended in chemotaxis assay buffer (HBSS supplemented with 0.1% BSA) at a density of $2 \times 10^6$ cells/ml. Cells were labeled with 1.0 μM Calcein AM for 40 minutes at 37° C., 5% $CO_2$. Following incubation, cells were washed once and re-suspended in assay buffer at a density of $2.0 \times 10^6$ cells/ml. Labeled cell suspension was added onto inserts (250 dl/well) and set aside. In a separate BD Falcon™ 48 well, flat-bottom plate, compound 1 or compound 2, (750 μl, 10 Mm) was added. The multiwell insert containing cells was gently lowered into the plate containing chemoattractant and immediately placed into a bottom fluorescence plate reader. Fluorescence emitted from cells that had migrated to the bottom surface of the insert was measured at various time points. Cells labeled with Calcein AM were read at 485/530 nm (Ex/Em) wavelength.

Monosodium urate crystal conditioned media was used. Compound 1 used at 10 μM. Compound 2 used at 10 μM.

Example 2C: Results

Figure 1B:
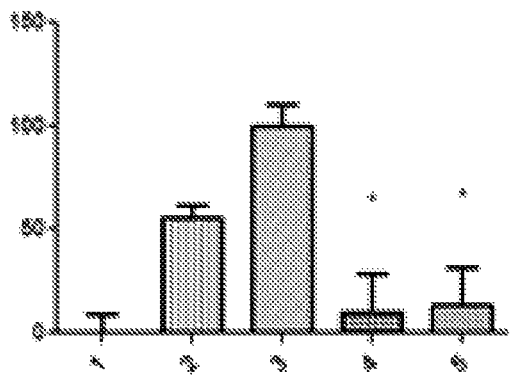
FIG. 1B depicts the PBMC counts.

The neutrophil counts are presented graphically in FIG. 1A, which shows Compound 1 and Compound 2 providing significant inhibition of migration in neutrophils (in the MSU-conditioned media). The PBMC counts are presented graphically in FIG. 1B, which shows Compounds 1 and 2 providing significant inhibition in migration in PBMCs.

Example 3: General Procedures for Rat Air Pouch Model of Crystal-Induced Arthropathy Example 3A: Preparation of Reagents Mono Sodium Urate (MSU):

Sodium hydroxide (40 g, Fisher Scientific) was dissolved in de-ionized water (100 mL, $dH_2O$) to provide a 10N solution. Uric acid (16 g, Sigma) was added to de-ionized water (3400 mL) containing sodium hydroxide solution (11.8 mL, 10N) and heated to 60° C. with constant stirring. The pH was adjusted to 8.9 with 10N sodium hydroxide solution. The resulting clear solution was cooled to 4-8° C., resulting in the formation of crystals, which were isolated by filtration, washed three times with de-ionized water (1 L) and dried at 37° C. The dried mono sodium urate crystals were sifted into an air-tight container for storage. Mono sodium urate (10 g) was suspended in sterile saline (1 L, 0.9%, USP, Hospira) for injection and placed on a stir plate to maintain a constant 10 mg/mL homogenous suspension.

Vehicle:

Methylcellulose (0.4 g, Sigma) was dissolved in de-ionized water (100 mL) to provide a 0.4% solution used as vehicle.

Colchicine:

Colchicine (7 mg, Sigma) was dissolved in sterile saline (7 mL) to provide a 1 mg/mL solution.

Heparinized Saline:

Heparinized saline (10 U/mL) was prepared by adding heparin (0.4 mL, 10,000 U/ml, APP Pharmaceuticals) to sterile sodium chloride solution (400 mL, 0.9%).

Test Compounds:

Test compounds were suspended in vehicle to provide the desired concentrations, and diluted accordingly. For example, test compound (102.5 mg) was suspended in vehicle (3.417 mL) to provide a 30 mg/mL suspension. 0.3 mL of the 30 mg/mL suspension was added to vehicle (2.7 mL) to provide a 3 mg/mL suspension. 0.3 mL of the 3 mg/mL suspension was added to vehicle (2.7 mL) to provide a 0.3 mg/mL suspension.

Example 3B: Rats

Male Sprague-Dawley rats (Charles River Laboratories, 160-180 g) were received, individually examined and housed in cages of five rats each. The animals were in apparent good health with no clinical signs of disease or distress. The rats were placed in quarantine with daily inspections, ear notched for identification purposes and shaved at the nape of the neck.

DAY 0:

The rats were anesthetized (isoflurane), and the nape of the neck was cleansed with 70% isopropanol (Butler Animal Health Supply) followed by povidone-iodine solution (Ricca Chemical Co.). Sterile air (30 mL, 0.2 μm, Millipore) was injected subcutaneously using a 23 G×1½ inch needle fixed to a 30 mL syringe. The rats were returned to routine housing with no adverse reactions observed.

DAY 3:

The rats were anesthetized (isoflurane), and the nape of the neck was cleansed with 70% isopropanol (Butler Animal Health Supply) followed by povidone-iodine solution (Ricca Chemical Co.). Sterile air (15 mL, 0.11 μm, Millipore) was injected subcutaneously using a 23 G×1½ inch needle fixed to a 20 mL syringe. The rats were returned to routine housing with no adverse reactions observed.

The rats were weighed and sorted into treatment groups based on average body weight.

As appropriate, the rats were dosed orally with test compound or vehicle (saline alone).

As appropriate, the rats were injected subcutaneously with colchicine (1 mL/kg).

As appropriate, the rats were dosed with test compound (oral administration) in combination with colchicine (injected subcutaneously).

Thirty minutes after SC injection or two hours after PO dosing, MSU (15 mL) was injected into the air pouch using an 18 G×2 inch needle fitted to a 20 mL syringe. Control group was injected with 15 mL sterile saline (vehicle). The injection sites were closed (collodion, Macron) and the rats returned to their cages with no adverse effects observed.

Example 3C: Samples

Four hours after MSU/saline injection, the rats were anesthetized and heparinized saline (5 mL, 10 U/mL) was injected into the air pouch. The air pouch was gently massaged, the contents immediately removed using a 14 G×1 inch needle fitted to a 6 mL syringe, and the exudate volume recorded. An aliquot of the exudate was transferred to green Eppendorf tubes for total white blood cell (WBC) measurement. After allowing the MSU crystals to settle out for ten minutes, an aliquot of the exudate was transferred to heparinized microtainer tubes (Becton Dickinson) for differential white blood cell counts. The remainder of the exudate was centrifuged and an aliquot of the supernatants was dispensed to labeled clear Eppendorf tubes and stored at −80° C. The rats were exsanguinated into pre-chilled serum separator tubes, processed to serum, and 0.5 mL aliquot was stored at −80° C. in labeled Eppendorf tubes.

Example 4: Compound 2 in Rat Air Pouch Model

Compound 2 was tested according to the protocol described in example 2. 60 rats were used, divided into 6 groups of 10 animals, as follows:

|  | Group | | | | | |
|---|---|---|---|---|---|---|
|  | 1 | 2 | 3 | 4 | 5 | 6 |
| Treatment | Vehicle | | Colchicine | Compound 2 | | |
| *ROA | PO | PO | SC (−2 Hr) | PO | PO | PO |
| Dose | 1 ml/kg | 1 ml/kg | 1 mg/kg | 0.3 mg/kg | 3.0 mg/kg | 30 mg/kg |

*ROA = route of administration—oral (PO) or subcutaneous injection (SC)

Figure 2A:
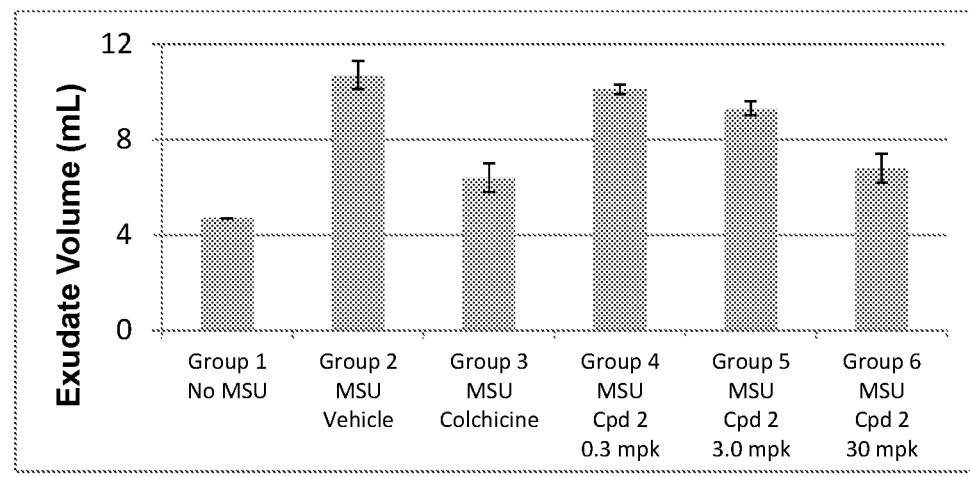
FIG. 2A depicts the average exudate volume.
Figure 2B:
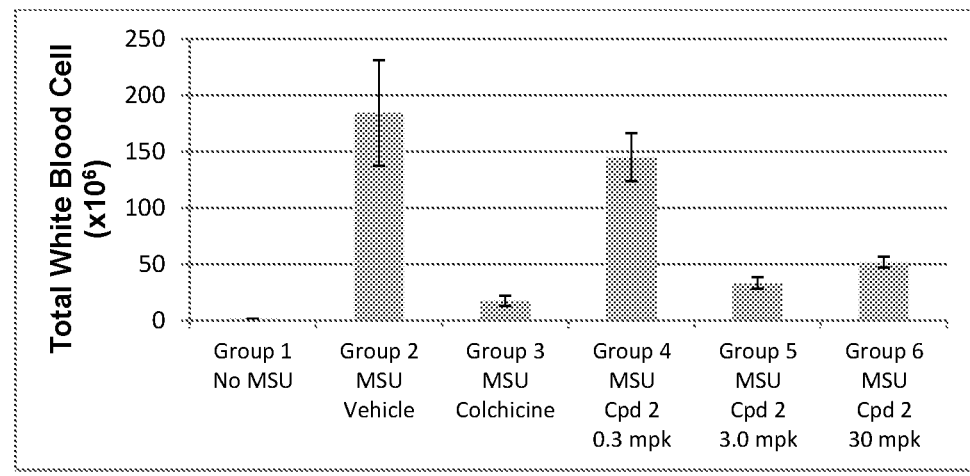
FIG. 2B depicts the total white blood cell counts.
Figure 2C:
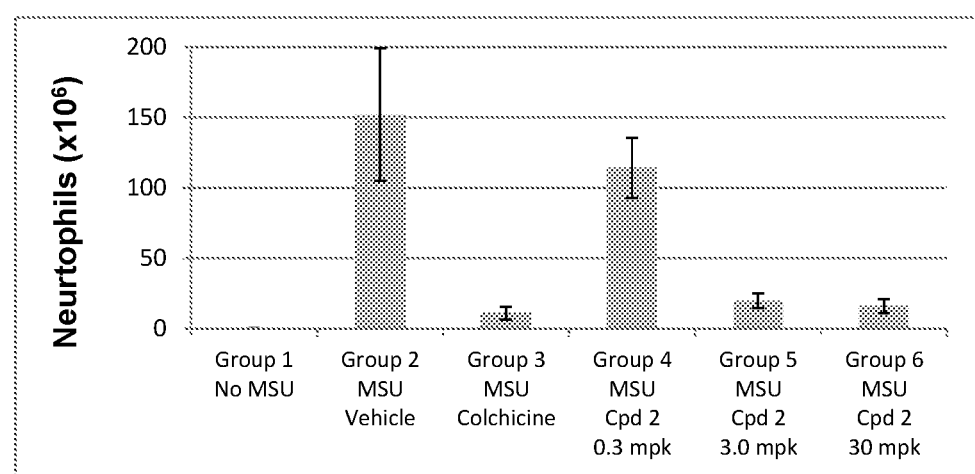
FIG. 2C depicts the neutrophil counts.

The results—average exudate volume (FIG. 2A), total white blood cell counts (FIG. 2B) and neutrophil counts (FIG. 2C) are provided in the table below and presented in FIG. 2.

|  | Group 1 | Group 2 | Group 3 | Group 4 | Group 5 | Group 6 |
|---|---|---|---|---|---|---|
| MSU | N | Y | Y | Y | Y | Y |
| Treatment |  | Vehicle | Colchicine | Compound 2 | | |
| Route of Admin. |  |  | SC | PO | PO | PO |
| Dose |  |  | 1 mg/kg | 0.3 mg/kg | 3 mg/kg | 30 mg/kg |
| Avg Exudate Vol (mL) | 4.7 | 10.7 | ***6.4 | 10.1 | 9.3 | ***6.8 |
| SE | 0.0 | 0.6 | 0.6 | 0.2 | 0.3 | 0.6 |
| Avg Total WBC (×$10^6$) | 1.7 | 184.5 | **17.6 | 145.2 | *33.4 | *51.7 |
| SE (×$10^6$) | 0.6 | 54.3 | 7.2 | 27.2 | 6.9 | 11.9 |
| Neutrophils (×$10^6$) | 0.3 | 152.0 | **11.0 | 114.2 | *19.8 | **16.0 |
| SE (×$10^6$) | 0.10 | 46.86 | 4.64 | 21.34 | 5.32 | 4.81 | p-test:
*** = $p < 0.001$;
** = $p < 0.05$;
* = $p < 0.01$

Example 5: Compound 2 in Combination with Colchicine in the Rat Air Pouch Model

Compound 2 was tested, in the presence and absence of colchicine, at various doses, according to the protocol described in Example 2. 90 rats were used, divided into 9 groups of 10 animals, as follows:

| Group | Treatment | Dose | ROA |
|---|---|---|---|
| 1 | Vehicle | 1 ml/kg | PO |
| 2 | Vehicle | 1 ml/kg | PO |
| 3 | Colchicine | 0.1 mg/kg | PO |
| 4 | Cpd 2 | 0.3 mg/kg | PO |
| 5 | Cpd 2 | 3.0 mg/kg | PO |
| 6 | Cpd 2 | 0.3 mg/kg | PO |
|   | Colchicine | 0.01 mg/kg | SC |
| 7 | Cpd 2 | 3.0 mg/kg | PO |
|   | Colchicine | 0.01 mg/kg | SC |
| 8 | Cpd 2 | 0.3 mg/kg | PO |
|   | Colchicine | 0.1 mg/kg | SC |
| 9 | Cpd 2 | 3.0 mg/kg | PO |
|   | Colchicine | 0.1 mg/kg | SC |

Figure 3A:
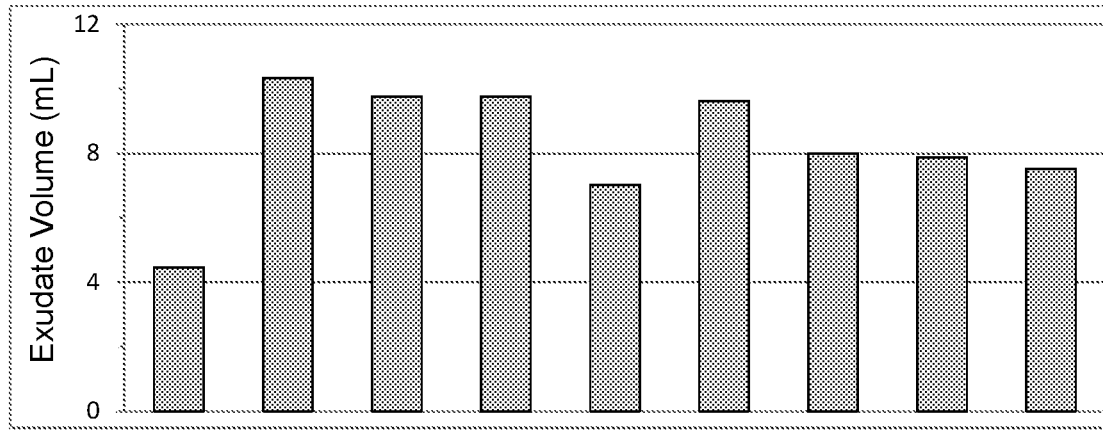
FIG. 3A depicts the average exudate volume.
Figure 3B:
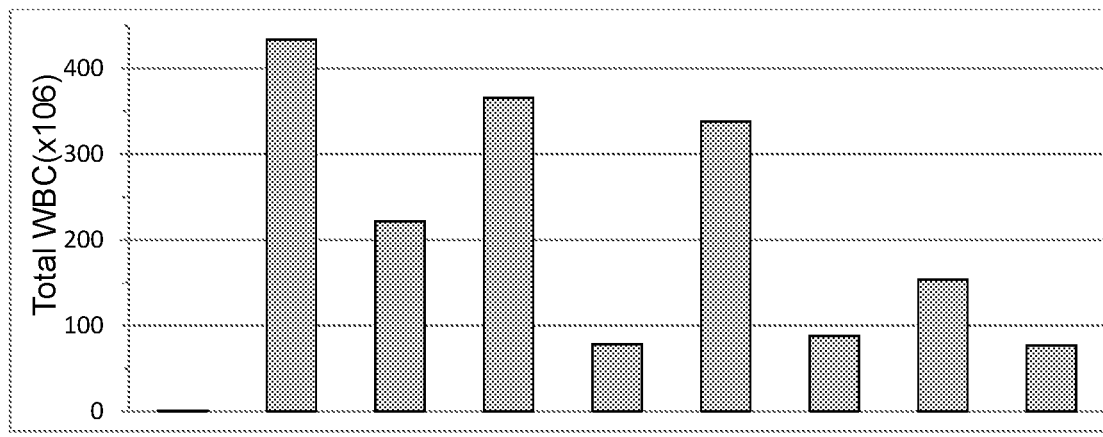
FIG. 3B depicts the total white blood cell counts.
Figure 3C:
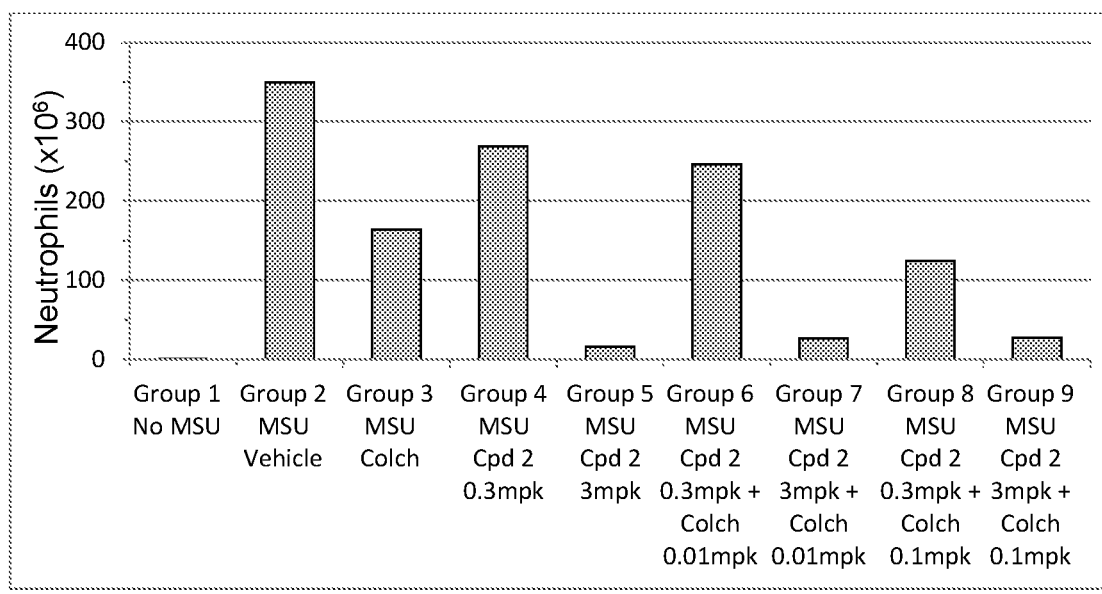
FIG. 3C depicts the neutrophil counts.

The results—average exudate volume (FIG. 3A), total white blood cell counts (FIG. 3B) and neutrophil counts (FIG. 3C) are provided in the table below and presented in FIG. 3.

| Gp | MSU | Treatment | Dose | Avg Exudate Vol (mL) | SE | Avg Total WBC ($\times 10^6$) | SE | Neutrophils ($\times 10^6$) | SE |
|---|---|---|---|---|---|---|---|---|---|
| 1 | N | Vehicle |  | 4.47 | 0.2 | 0.7 | 0.6 | 0.2 | 0.3 |
| 2 | Y | Vehicle |  | 10.3 | 1.4 | 433 | 492.8 | 349 | 442 |
| 3 | Y | Colchicine | 0.1 mpk | 9.7 | 0.6 | 221 | 52.1 | 163 | 55.9 |
| 4 | Y | Cpd 2 | 0.3 umol/kg | 9.8 | 1.1 | 365 | 249.2 | 268 | 182.7 |
| 5 | Y | Cpd 2 | 3.0 umol/kg | 7.0 | 2.3 | 78.6 | 124.4 | 16 | 23.2 |
| 6 | Y | Cpd 2 Colchicine | 0.3 umol/kg 0.001 mpk | 9.6 | 1.8 | 337 | 282.4 | 246 | 216.9 |
| 7 | Y | Cpd 2 Colchicine | 3.0 umol/kg 0.001 mpk | 8 | 1.2 | 88 | 72.4 | 26.7 | 15.8 |
| 8 | Y | Cpd 2 Colchicine | 0.3 umol/kg 0.1 mpk | 7.9 | 1.7 | 153 | 97.2 | 123 | 77.5 |
| 9 | Y | Cpd 2 Colchicine | 3.0 umol/kg 0.1 mpk | 7.5 | 1.3 | 76.8 | 47.6 | 27.2 | 32 |

Example 6: Compound 2, Compound 3 & Compound 4 in the Rat Air Pouch Model

Compounds 2, 3 and 4 were tested according to the protocol described in Example 2. 100 rats were used, divided into 10 groups of 10 animals, as follows:

| Group | Treatment | Dose | ROA |
|---|---|---|---|
| 1 | Vehicle | 10 ml/kg | PO |
| 2 | Vehicle | 10 ml/kg | PO |
| 3 | Cpd 2 | 3 mg/kg | PO |
| 4 | Colchicine | 1 mg/kg | SC |
| 5 | Cpd 3 | 0.3 μmole/kg | PO |
| 6 | Cpd 3 | 3 μmole/kg | PO |
| 7 | Cpd 3 | 30 μmole/kg | PO |
| 8 | Cpd 4 | 1 μmole/kg | PO |
| 9 | Cpd 4 | 30 μmole/kg | PO |
| 10 | Cpd 4 | 100 μmole/kg | PO |

Figure 4A:
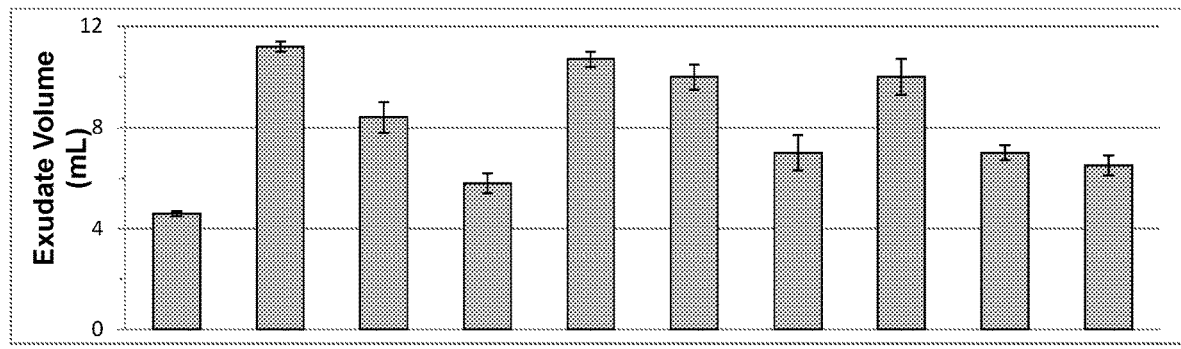
FIG. 4A depicts the average exudate volume.
Figure 4B:
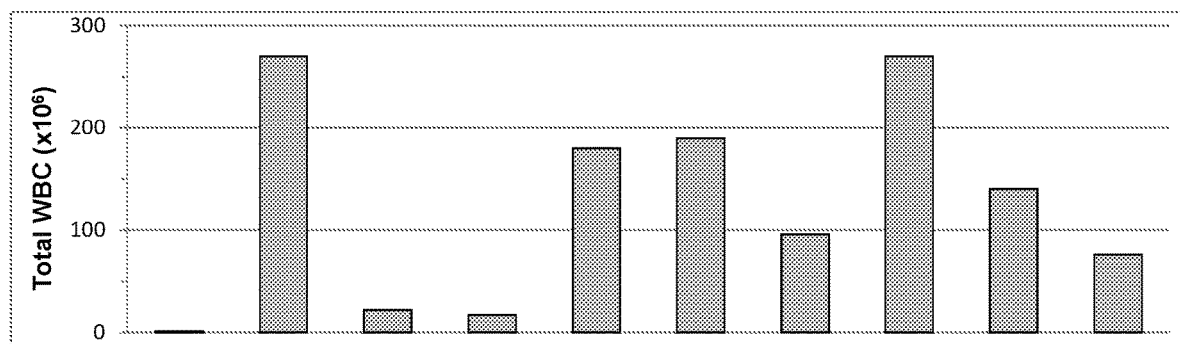
FIG. 4B depicts the total white blood cell counts.
Figure 4C:
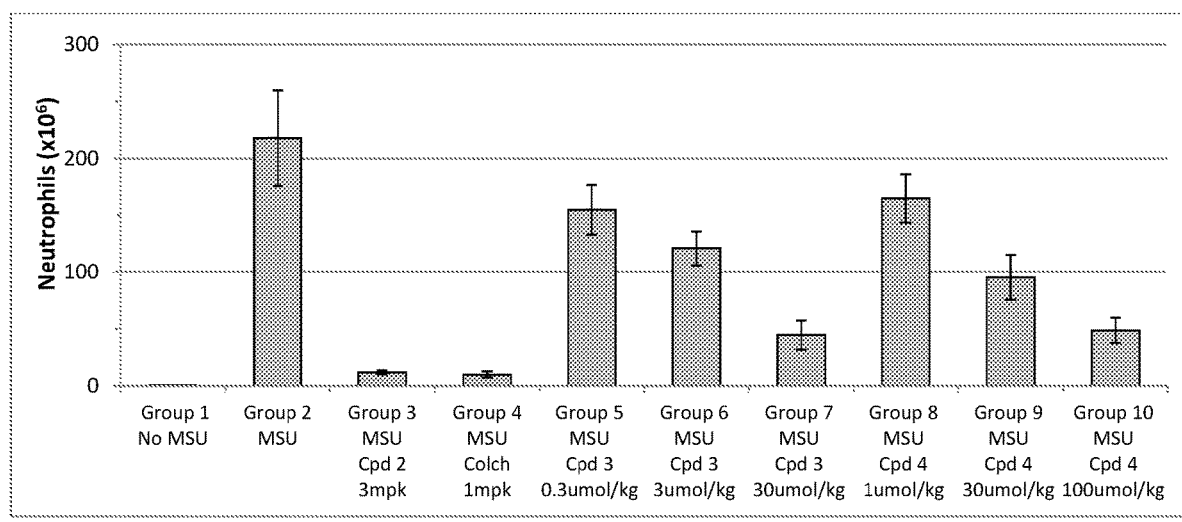
FIG. 4C depicts the neutrophil counts.

The results—average exudate volume (FIG. 4A), total white blood cell counts (FIG. 4B) and neutrophil counts (FIG. 4C) are provided in the table below and presented in FIG. 4.

| Gp | MSU | Treatment | Dose | Avg Exudate Vol (mL) | SE | Avg Total WBC (×10$^6$) | SE | Neutrophils (×10$^6$) | SE |
|---|---|---|---|---|---|---|---|---|---|
| 1 | N | Vehicle | | 4.6 | 0.1 | 1.1 | 0.21 | 0.25 | 0.05 |
| 2 | Y | Vehicle | | 11.2 | 0.2 | 270 | 45 | 218 | 42 |
| 3 | Y | Cpd 2 | 3 mpk | 8.4 | 0.6 | 22 | 2.7 | 11.8 | 1.7 |
| 4 | Y | Colchicine | 1 mpk | 5.8 | 0.4 | 17 | 3.8 | 9.9 | 2.5 |
| 5 | Y | Cpd 3 | 0.3 umol/kg | 10.7 | 0.3 | 180 | 23 | 155 | 22 |
| 6 | Y | Cpd 3 | 3.0 umol/kg | 10 | 0.5 | 190 | 21 | 121 | 15 |
| 7 | Y | Cpd 3 | 30.0 umol/kg | 7 | 0.7 | 96 | 33 | 44.6 | 13 |
| 8 | Y | Cpd 4 | 1.0 umol/kg | 10 | 0.7 | 270 | 62 | 165 | 21 |
| 9 | Y | Cpd 4 | 30 umol/kg | 7 | 0.3 | 140 | 27 | 95.4 | 20 |
| 10 | Y | Cpd 4 | 100 umol/kg | 6.5 | 0.4 | 76 | 19 | 48.6 | 11 |

Example 7: Compound 3 and Compound 4 in Combination with Colchicine in the Rat Air Pouch Model Compounds 3 and 4 were tested, in the presence and absence of colchicine, at various doses, according to the protocol described in Example 2. 100 rats were used, divided into 10 groups of 10 animals, as follows:

| Group | Treatment | Dose | ROA |
|---|---|---|---|
| 1 | Vehicle | 10 ml/kg | PO |
| 2 | Vehicle | 10 ml/kg | PO |
| 3 | Colchicine | 0.1 mg/kg | SC |
| 4 | Colchicine | 1.0 mg/kg | SC |
| 5 | Cpd 3 | 3 μmole/kg | PO |
| 6 | Cpd 3 | 30 μmole/kg | PO |
| 7 | Cpd 4 | 1 μmole/kg | PO |
| 8 | Cpd 4 | 30 μmole/kg | PO |
| 9 | Cpd 4 | 1 μmole/kg | PO |
|   | Colchicine | 0.1 mg/kg | SC |
| 10 | Cpd 3 | 3 μmole/kg | PO |
|   | Colchicine | 0.1 mg/kg | SC |

Figure 5A:
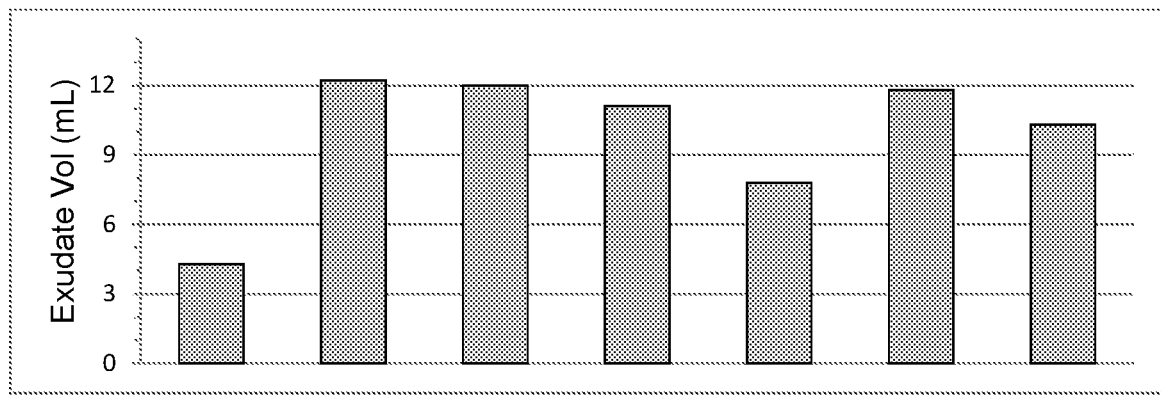
FIG. 5A depicts the average exudate volume.
Figure 5B:
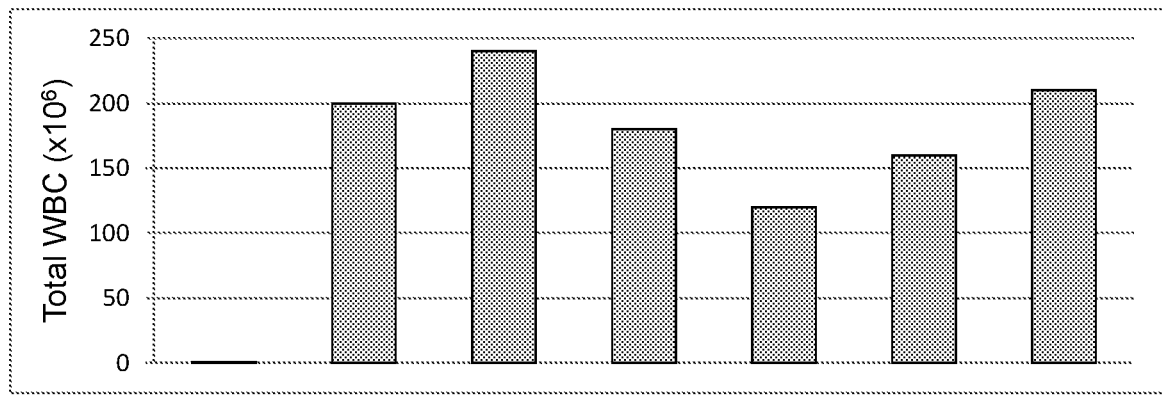
FIG. 5B depicts the total white blood cell counts.
Figure 5C:
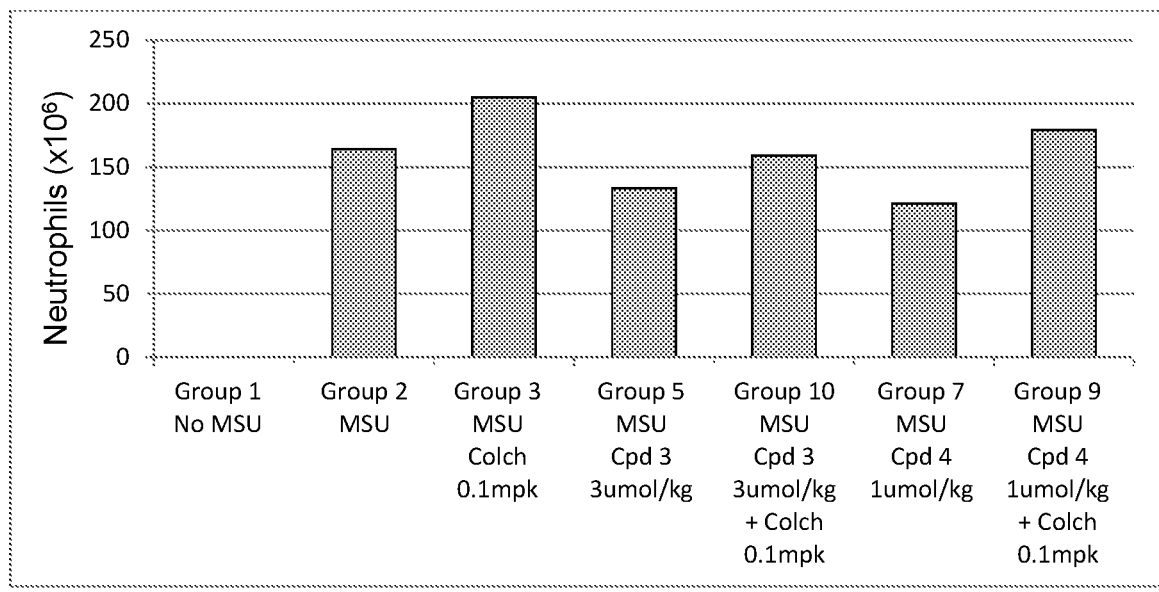
FIG. 5C depicts the neutrophil counts.

The results—average exudate volume (FIG. 5A), total white blood cell counts (FIG. 5B) and neutrophil counts (FIG. 5C) are provided in the table below and presented in FIG. 5.

| Gp | MSU | Treatment | Dose | Avg Exudate Vol (mL) | SE | Avg Total WBC (×10$^6$) | SE | Neutrophils (×10$^6$) | SE |
|---|---|---|---|---|---|---|---|---|---|
| 1 | N | Vehicle | | 4.3 | 0 | 0.9 | 0.2 | 0.2 | 0.06 |
| 2 | Y | Vehicle | | 12.2 | 0.3 | 200 | 23 | 164 | 20 |
| 3 | Y | Colchicine | 0.1 mpk | 12 | 0.4 | 240 | 34 | 205 | 32 |
| 4 | Y | Colchicine | 1.0 mpk | 6 | 0.4 | 22 | 7.7 | 10.8 | 2.9 |
| 5 | Y | Cpd 3 | 3 umol/kg | 11.1 | 0.4 | 180 | 55 | 133 | 33 |
| 6 | Y | Cpd 3 | 30 umol/kg | 7.4 | 0.5 | 110 | 28 | 65.2 | 19 |
| 7 | Y | Cpd 4 | 1 umol/kg | 11.8 | 0.4 | 160 | 30 | 121 | 22 |
| 8 | Y | Cpd 4 | 30 umol/kg | 8.1 | 0.5 | 100 | 29 | 69.6 | 19 |
| 9 | Y | Cpd 4 | 1 umol/kg | 10.3 | 0.3 | 210 | 45 | 179 | 41 |
|   |   | Colchicine | 0.1 mpk | | | | | | |
| 10 | Y | Cpd 3 | 3.0 umol/kg | 7.8 | 0.5 | 120 | 34 | 159 | 38 |
|   |   | Colchicine | 0.1 mpk | | | | | | |

Example 8: Compound 3 in Combination with Colchicine in the Rat Air Pouch Model Compounds 3 was tested, in the presence and absence of colchicine, at various doses, according to the protocol described in Example 2. 100 rats were used, divided into 10 groups of 10 animals, as follows:

| Group | Treatment | Dose | ROA |
|---|---|---|---|
| 1 | Vehicle | 10 ml/kg | PO |
| 2 | Vehicle | 10 ml/kg | PO |
| 3 | Colchicine | 0.3 mg/kg | SC |
| 4 | Colchicine | 0.5 mg/kg | SC |
| 5 | Colchicine | 1.0 mg/kg | SC |
| 6 | Cpd 3 | 10 μmol/kg | PO |
| 7 | Cpd 3 | 30 μmol/kg | PO |
| 8 | Cpd 3 | 100 μmol/kg | PO |
| 9 | Cpd 3 | 300 μmol/kg | PO |
| 10 | Cpd 3 | 10 μmole/kg | PO |
|  | Colchicine | 0.3 mg/kg | SC |

Figure 6A:
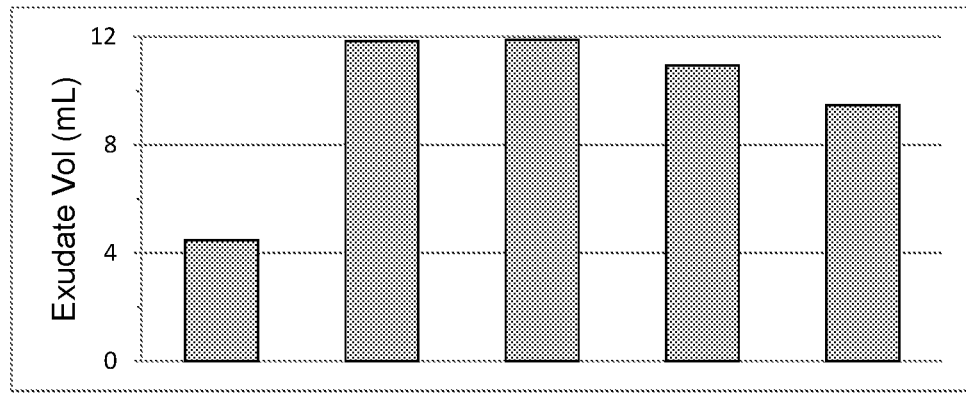
FIG. 6A depicts the average exudate volume.
Figure 6B:
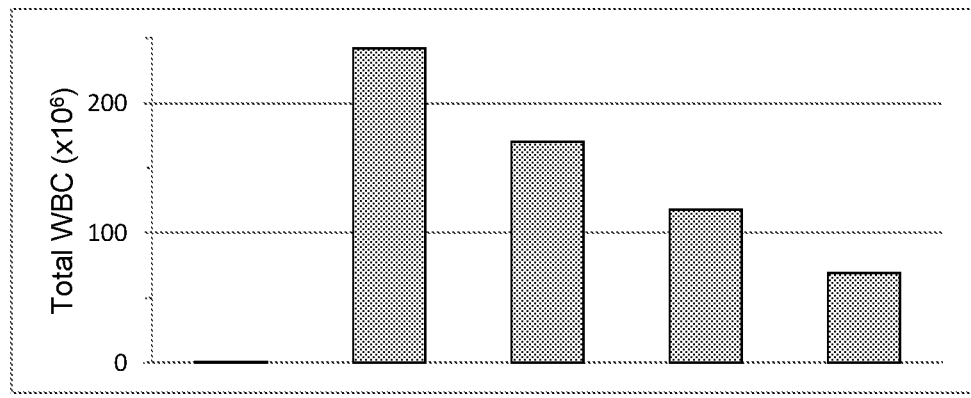
FIG. 6B depicts the total white blood cell counts.
Figure 6C:
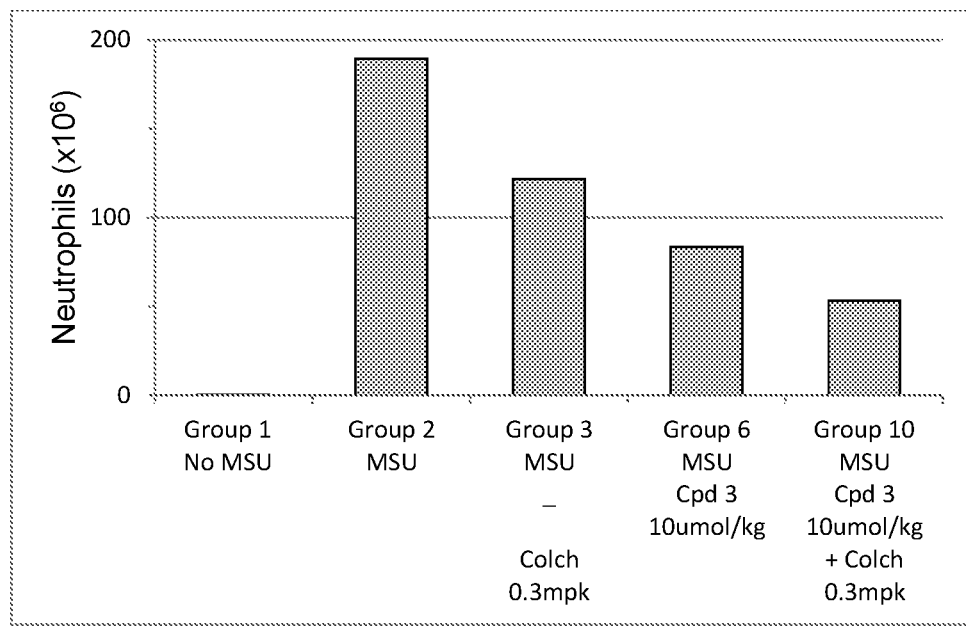
FIG. 6C depicts the neutrophil counts.

The results—average exudate volume (FIG. 6A), total white blood cell counts (FIG. 6B) and neutrophil counts (FIG. 6C) are provided in the table below and presented in FIG. 6 (Groups 1, 2, 3, 6 and 10).

| Gp | MSU | Treatment | Dose | Avg Exudate Vol (mL) | SE | Avg Total WBC ($\times 10^6$) | SE | Neutrophils ($\times 10^6$) | SE |
|---|---|---|---|---|---|---|---|---|---|
| 1 | N | Vehicle |  | 4.47 | 0.1 | 0.8 | 0.2 | 0.14 | 0.05 |
| 2 | Y | Vehicle |  | 11.84 | 0.3 | 242 | 31.9 | 189.3 | 21.4 |
| 3 | Y | Colchicine | 0.3 mpk | 11.88 | 0.3 | 170 | 64.3 | 121.8 | 51.9 |
| 4 | Y | Colchicine | 0.5 mpk | 7.62 | 0.1 | 96.3 | 28.2 | 64.6 | 18.2 |
| 5 | Y | Colchicine | 1.0 mpk | 6.8 | 0.2 | 41.5 | 13.9 | 7.6 | 2.9 |
| 6 | Y | Cpd 3 | 10.0 umol/kg | 10.93 | 0.4 | 118 | 30.3 | 83.3 | 24.4 |
| 7 | Y | Cpd 3 | 30.0 umol/kg | 8.42 | 0.3 | 70.5 | 20.3 | 40.3 | 13.6 |
| 8 | Y | Cpd 3 | 100 umol/kg | 6.56 | 0.2 | 56.1 | 18.8 | 25.2 | 10.5 |
| 9 | Y | Cpd 3 | 300 umol/kg | 5.7 | 0.3 | 24.7 | 10.7 | 5.3 | 3.8 |
| 10 | Y | Cpd 3 Colchicine | 10.0 umol/kg 0.3 mpk | 9.46 | 0.6 | 69.1 | 26.9 | 53.1 | 20.4 |

Example 9: Compound 4 in Combination with Colchicine in the Rat Air Pouch Model Compound 4 was tested, in the presence and absence of colchicine, at various doses, according to the protocol described in Example 2. 100 rats were used, divided into 10 groups of 10 animals, as follows:

| Group | Treatment | Dose (mg/kg) | ROA |
|---|---|---|---|
| 1 | Vehicle | 10 ml/kg | PO |
| 2 | Vehicle | 10 ml/kg | PO |
| 3 | Colchicine | 0.3 mg/kg | SC |
| 4 | Colchicine | 0.5 mg/kg | SC |
| 5 | Colchicine | 1.0 mg/kg | SC |
| 6 | Cpd 4 | 10 μmol/kg | PO |
| 7 | Cpd 4 | 30 μmol/kg | PO |
| 8 | Cpd 4 | 100 μmol/kg | PO |
| 9 | Cpd 4 | 300 μmol/kg | PO |
| 10 | Cpd 4 | 10 μmole/kg | PO |
|  | Colchicine | 0.3 mg/kg | SC |

Figure 7A:
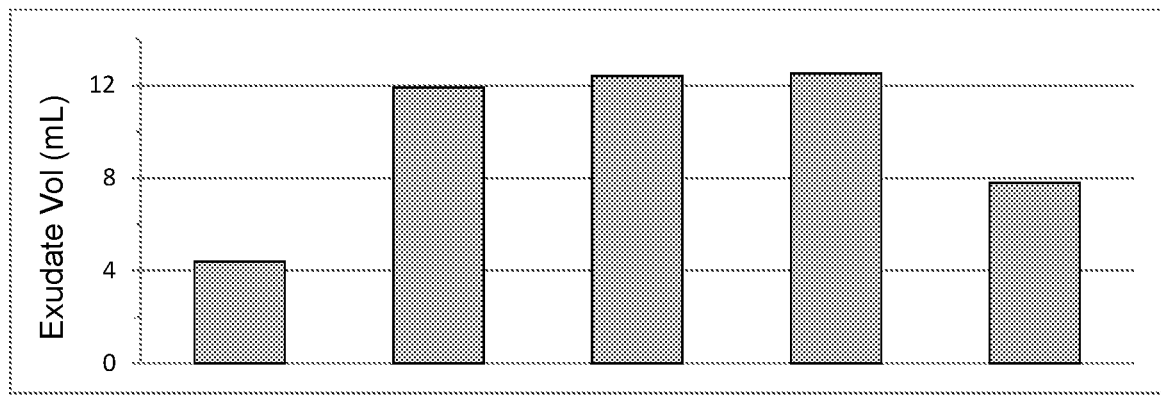
FIG. 7A depicts the average exudate volume.
Figure 7B:
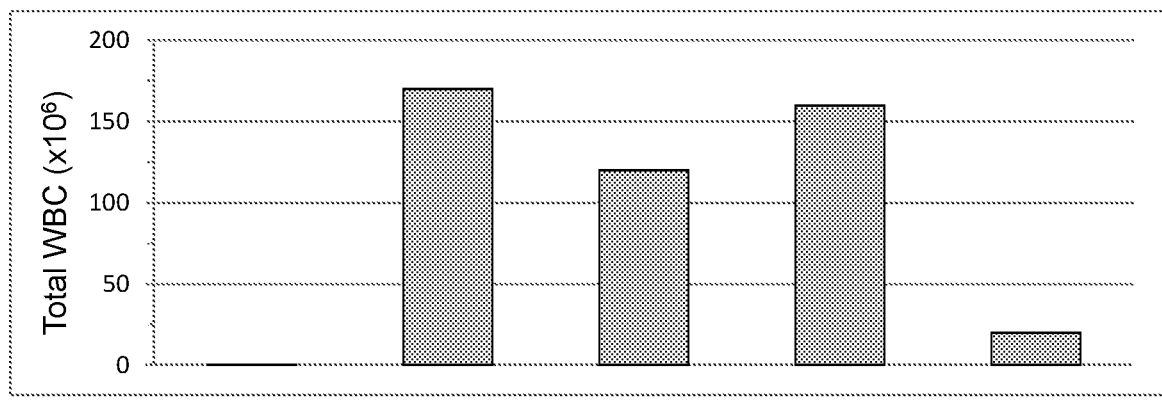
FIG. 7B depicts the total white blood cell counts.
Figure 7C:
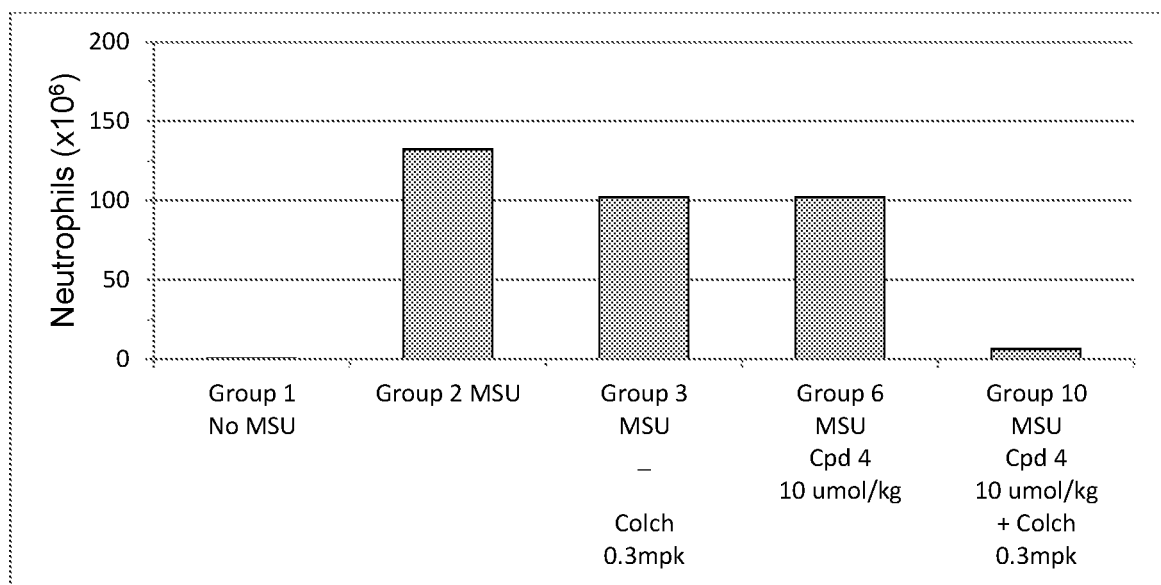
FIG. 7C depicts the neutrophil counts.

The results—average exudate volume (FIG. 7A), total white blood cell counts (FIG. 7B) and neutrophil counts (FIG. 7C) are provided in the table below and presented in FIG. 7 (Groups 1, 2, 3, 6 and 10).

| Gp | MSU | Treatment | Dose | Avg Exudate Vol (mL) | SE | Avg Tot WBC (×10⁶) | SE | Neutrophils (×10⁶) | SE |
|---|---|---|---|---|---|---|---|---|---|
| 1 | N | Vehicle | | 4.4 | 0.1 | 0.3 | 0.2 | 0.09 | 0.02 |
| 2 | Y | Vehicle | | 11.9 | 0.5 | 170 | 39 | 132.2 | 34.7 |
| 3 | Y | Colchicine | 0.3 mpk | 12.4 | 0.4 | 120 | 13.9 | 101.9 | 13.7 |
| 4 | Y | Colchicine | 0.5 mpk | 8.8 | 0.5 | 58 | 10.6 | 42.7 | 8.8 |
| 5 | Y | Colchicine | 1.0 mpk | 5.6 | 0.2 | 16 | 5.9 | 9.8 | 4.1 |
| 6 | Y | Cpd 4 | 10.0 umol/kg | 12.5 | 0.5 | 160 | 40.4 | 102.1 | 29.4 |
| 7 | Y | Cpd 4 | 30.0 umol/kg | 6.7 | 0.4 | 28.7 | 17.5 | 14 | 8.4 |
| 8 | Y | Cpd 4 | 100 umol/kg | 6 | 0.3 | 12 | 6.4 | 3.8 | 1.9 |
| 9 | Y | Cpd 4 | 300 umol/kg | 5.2 | 0.2 | 8.1 | 4.5 | 4.3 | 3.1 |
| 10 | Y | Cpd 4 Colchicine | 10 umol/kg 0.3 mpk | 7.8 | 0.4 | 20 | 8.7 | 6.4 | 2.9 |

Example 10: Compound 3 and Compound 4 in Combination with Colchicine in a Therapeutic Model Compounds 3 and 4 were tested, in the presence and absence of colchicine, at various doses, according to the protocol described in Example 2. 140 rats were used, divided into 14 groups of 10 animals, as follows:

| Group | Treatment | Dose | ROA |
|---|---|---|---|
| 1 | Vehicle | N/A | PO |
| 2 | Vehicle | N/A | PO |
| 3 | Colchicine | 0.3 mg/kg | SC |
| 4 | Colchicine | 0.5 mg/kg | SC |
| 5 | Colchicine | 1.0 mg/kg | SC |
| 6 | Cpd 4 | 10 μmol/kg | PO |
| 7 | Cpd 4 | 30 μmol/kg | PO |
| 8 | Cpd 4 | 100 μmol/kg | PO |
| 9 | Cpd 4 Colchicine | 10 μmole/kg 0.3 mg/kg | PO SC |
| 10 | Cpd 3 | 3 μmol/kg | PO |
| 11 | Cpd 3 | 10 μmol/kg | PO |
| 12 | Cpd 3 | 30 μmol/kg | PO |
| 13 | Cpd 3 | 100 μmol/kg | PO |
| 14 | Cpd 3 Colchicine | 10 μmol/kg 0.3 mg/kg | PO SC |

Figure 8A:
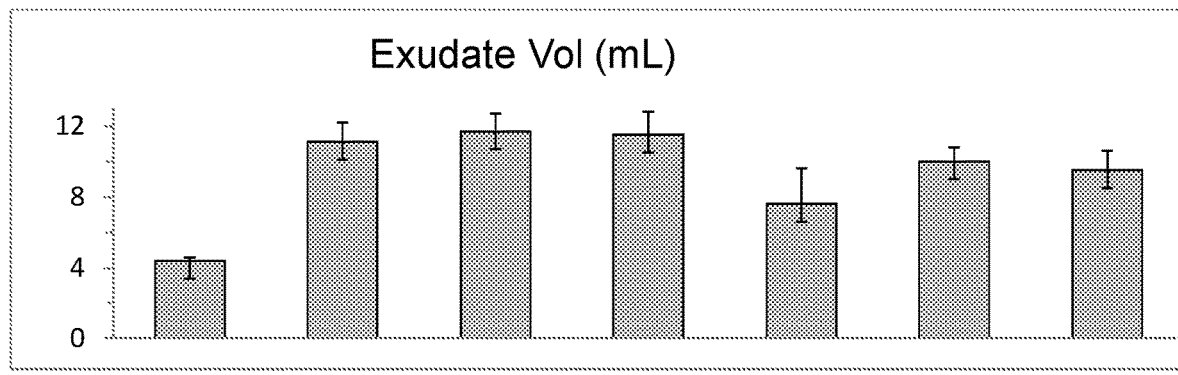
FIG. 8A depicts the average exudate volume.
Figure 8B:
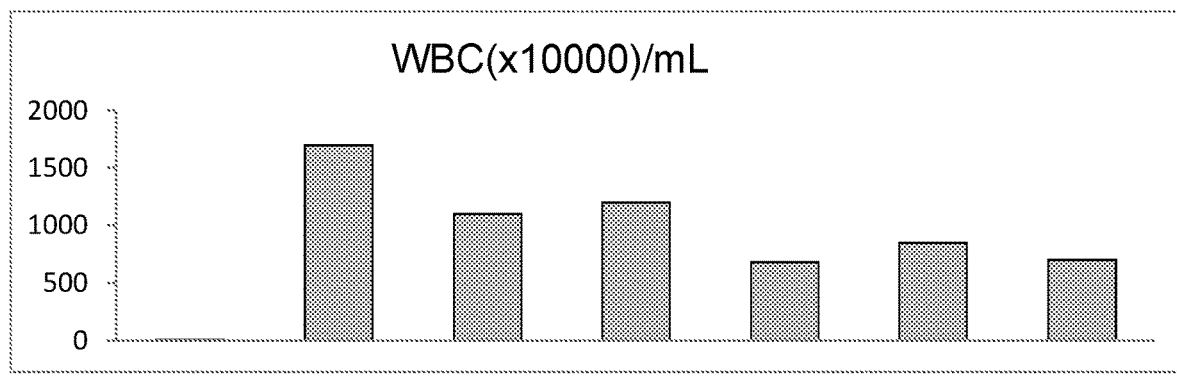
FIG. 8B depicts the total white blood cell counts.
Figure 8C:
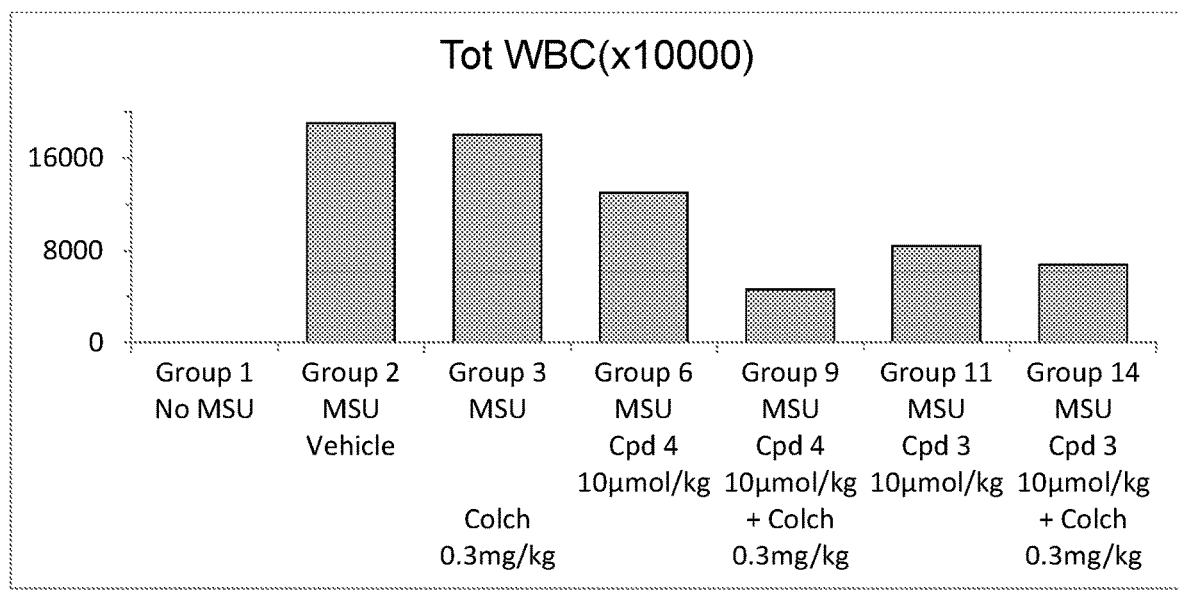
FIG. 8C depicts the neutrophil counts.

The results—average exudate volume (FIG. 8A), total white blood cell counts (FIG. 8B) and neutrophil counts (FIG. 8C) are provided in the table below and presented in FIG. 8 (Groups 1, 2, 3, 6, 9, 11 & 14).

| Gp | MSU | Treatment | Dose | Avg Exudate Vol (mL) | SE | Avg Tot WBC (×10⁶) | Neutrophils (×10⁶) | SE |
|---|---|---|---|---|---|---|---|---|
| 1 | N | Vehicle | | 4.4 | 0.2 | 0.38 | 26.9 | 8.1 |
| 2 | Y | Vehicle | | 11.1 | 1.1 | 190 | 81.5 | 4.9 |
| 3 | Y | Colchicine | 0.3 mpk | 11.7 | 1.0 | 180 | 71.5 | 3.8 |
| 4 | Y | Colchicine | 0.5 mpk | 8.9 | 1.2 | 35 | 70.7 | 5.2 |
| 5 | Y | Colchicine | 1.0 mpk | 7.3 | 1.1 | 9.8 | 25.9 | 7.5 |
| 6 | Y | Cpd 4 | 10 μmol/kg | 11.5 | 1.3 | 130 | 68.4 | 7.6 |
| 7 | Y | Cpd 4 | 30 μmol/kg | 8.2 | 1.6 | 25 | 60.4 | 7.2 |
| 8 | Y | Cpd 4 | 100 μmol/kg | 7.0 | 1.6 | 18 | 26.2 | 6.4 |
| 9 | Y | Cpd 4 Colchicine | 10 μmole/kg 0.3 mg/kg | 7.6 | 2.0 | 46 | 61.5 | 6.4 |
| 10 | Y | Cpd 3 | 3 μmol/kg | 11.5 | 1.2 | 120 | 71.1 | 3.1 |
| 11 | Y | Cpd 3 | 10 μmol/kg | 10.0 | 0.8 | 84 | 69.2 | 4.9 |
| 12 | Y | Cpd 3 | 30 μmol/kg | 8.8 | 1.8 | 59 | 30.7 | 9.3 |
| 13 | Y | Cpd 3 | 100 μmol/kg | 6.9 | 1.4 | 40 | 35.1 | 8.9 |
| 14 | Y | Cpd 3 Colchicine | 10 μmol/kg 0.3 mg/kg | 9.5 | 1.1 | 68 | 72.6 | 2.7 |

What is claimed is:

1. A method for treating or preventing a gout flare or the incidence of a gout flare, comprising concomitantly or sequentially administering colchicine to a subject in need thereof in combination with an effective amount of:
N-(6-(((2R,3S)-3,4-dihydroxy butan-2-yl)oxy)-2-((4-fluoro benzyl)thio)pyrimidin-4-yl)-3-methylazetidine-1-sulfonamide:

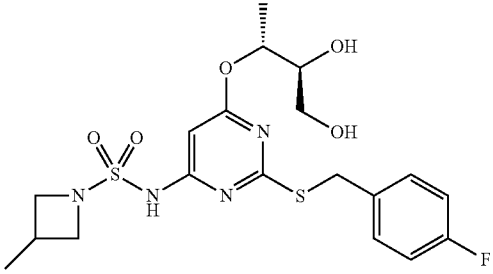 [SMILES: CC1CN(S(=O)(=O)Nc2cc(O[C@H](C)[C@@H](O)CO)nc(SCc3ccc(F)cc3)n2)C1]

or a pharmaceutically acceptable salt thereof.

2. The method of claim 1, wherein the treating comprises increasing the rapidity of relief of symptoms of the gout flare in the subject.

3. The method of claim 1, wherein the treating comprises reducing the duration or intensity of the gout flare in the subject.

4. The method of claim 1, wherein the gout flare is associated with gout therapy.

5. The method of claim 4, wherein gout therapy comprises treatment with a xanthine oxidase inhibitor, a URAT1 inhibitor, a uricosuric agent, a urate oxidase enzyme, a PNP inhibitor, a SGLT2 inhibitor, or a combination thereof.

6. The method of claim 4, wherein the gout therapy is selected from allopurinol, febuxostat, uricase, pegylated uricase, rasburicase, probenecid, sulfinpyrazone, benzbromarone, fenofibrate, lesinurad, zurampic, verinurad, arhalofenate, oral bucillamine or combinations thereof.

7. The method of claim 1, wherein the gout flare is an acute gout flare.

8. The method of claim 1, wherein the subject is an adult.

9. The method of claim 1, wherein the combination is a synergistic combination.

10. The method of claim 1, comprising administering less than about 1.2 mg colchicine per day.

11. The method of claim 1, comprising administering less than about 0.6 mg colchicine per day.

* * * * *

UNITED STATES PATENT AND TRADEMARK OFFICE
CERTIFICATE OF CORRECTION

PATENT NO. : 10,772,886 B2  
APPLICATION NO. : 15/516465  
DATED : September 15, 2020  
INVENTOR(S) : Nanavati et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 195 days.

Signed and Sealed this  
Twenty-third Day of November, 2021

Drew Hirshfeld  
*Performing the Functions and Duties of the*  
*Under Secretary of Commerce for Intellectual Property and*  
*Director of the United States Patent and Trademark Office*